(12) United States Patent
Scheunemann et al.

(10) Patent No.: US 10,945,941 B2
(45) Date of Patent: Mar. 16, 2021

(54) POWERFUL HAIR TREATMENT AGENT WITH ANTI-WASHOUT EFFECT

(71) Applicant: Henkel AG & Co. KGaA, Duesseldorf (DE)

(72) Inventors: Volker Scheunemann, Lueneburg (DE); Erik Schulze zur Wiesche, Hamburg (DE); Rene Krohn, Norderstedt (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 203 days.

(21) Appl. No.: 15/365,163

(22) Filed: Nov. 30, 2016

(65) Prior Publication Data

US 2017/0151153 A1 Jun. 1, 2017

(30) Foreign Application Priority Data

Dec. 1, 2015 (DE) .................. 10 2015 223 842.3

(51) Int. Cl.
| | | |
|---|---|---|
| *A61K 8/73* | (2006.01) | |
| *A61Q 5/00* | (2006.01) | |
| *A61Q 5/12* | (2006.01) | |
| *A61K 8/34* | (2006.01) | |
| *A61K 8/19* | (2006.01) | |
| *A61K 8/25* | (2006.01) | |
| *A61K 8/36* | (2006.01) | |
| *A61K 8/362* | (2006.01) | |
| *A61K 8/365* | (2006.01) | |
| *A61K 8/41* | (2006.01) | |

(52) U.S. Cl.
CPC .............. *A61K 8/731* (2013.01); *A61K 8/19* (2013.01); *A61K 8/25* (2013.01); *A61K 8/34* (2013.01); *A61K 8/342* (2013.01); *A61K 8/36* (2013.01); *A61K 8/362* (2013.01); *A61K 8/365* (2013.01); *A61K 8/416* (2013.01); *A61Q 5/004* (2013.01); *A61Q 5/12* (2013.01); *A61K 2800/5426* (2013.01); *A61K 2800/594* (2013.01); *A61K 2800/596* (2013.01); *A61K 2800/5922* (2013.01)

(58) Field of Classification Search
None
See application file for complete search history.

(56) References Cited

U.S. PATENT DOCUMENTS

| | | | | |
|---|---|---|---|---|
| 5,788,956 | A * | 8/1998 | De Lacharriere | A61K 8/19 424/400 |
| 2006/0089342 | A1* | 4/2006 | Gavin | A61K 31/555 514/184 |
| 2006/0115440 | A1* | 6/2006 | Arata | A61K 8/19 424/65 |
| 2009/0214628 | A1* | 8/2009 | de Rijk | A61K 9/127 424/450 |
| 2010/0055060 | A1* | 3/2010 | Yoshida | A61K 8/345 424/64 |

FOREIGN PATENT DOCUMENTS

| | | | | |
|---|---|---|---|---|
| DE | 102007009333 A1 * | 8/2008 | | A61Q 7/00 |
| EP | 2438900 A1 | 4/2012 | | |
| JP | 201251845 | * | 3/2012 | A61K 8/97 |
| WO | WO2010003627 | * | 1/2010 | A61Q 15/00 |
| WO | WO2010145922 | * | 12/2010 | A61K 8/04 |

OTHER PUBLICATIONS

WO2010003627 Eng. Tran. Published: Jan. 2010.*
DE102007009333 Eng Tran. Published: Aug. 2008.*
U.S. Appl. No. 15/358,889, filed Nov. 22, 2016.
Preliminary Amendment for U.S. Appl. No. 15/358,889, filed Nov. 22, 2016.
U.S. Appl. No. 15/359,040, filed Nov. 22, 2016.
Preliminary Amendment for U.S. Appl. No. 15/359,040, filed Nov. 22, 2016.
U.S. Appl. No. 15/360,285, filed Nov. 23, 2016.
Preliminary Amendment for U.S. Appl. No. 15/360,285, filed Nov. 23, 2016.
U.S. Appl. No. 15/359,006, filed Nov. 22, 2016.
Preliminary Amendment for U.S. Appl. No. 15/359,006, filed Nov. 22, 2016.

* cited by examiner

*Primary Examiner* — Nicole P Babson
*Assistant Examiner* — Lori K Mattison
(74) *Attorney, Agent, or Firm* — Lorenz & Kopf, LLP

(57) ABSTRACT

Hair treatment agents are provided herein. The hair treatment agent contains at least one fatty alcohol; at least one cationic surfactant; at least one divalent or trivalent metal salt; at least one silver salt selected from silver acetate, silver adipate, silver citrate, silver galactarate, silver gluconate, silver lactate, silver malate, silver mandelate, silver salicylate, silver succinate, silver sulfate, and silver tartrate; and at least one organic acid selected from adipic acid, succinic acid, citric acid, acetic acid, galactaric acid, gluconic acid, hydroxysuccinic acid, mandelic acid, lactic acid, salicylic acid, sulfuric acid, and tartaric acid. The hair treatment agent reduces or prevents the fading of color from dyed hair.

2 Claims, No Drawings

Specification includes a Sequence Listing.

POWERFUL HAIR TREATMENT AGENT WITH ANTI-WASHOUT EFFECT

CROSS-REFERENCE TO RELATED APPLICATION

This application claims priority to German Patent Application No. 10 2015 223 842.3, filed Dec. 1, 2015, which is incorporated herein by reference in its entirety.

TECHNICAL FIELD

The disclosure relates to hair treatment agents, in particular shampoos and so-called conditioners, having an active ingredient combination for gentle and effective hair care. The importance of hair care products with the longest-lasting effect possible has been increasing not least of all due to the great stress on hair, for example, due to dyeing or permanent waves as well as due to shampooing hair and exposure to environmental pollutants. Such care agents influence the natural structure and properties of hair. Thus, for example, the wet and dry combability of hair, the hold and fullness of hair can be optimized following such care treatments or the hair can be protected from increased split ends.

BACKGROUND

It has therefore been customary for a long time to subject hair to a special after-treatment in which the hair is treated with special active ingredients, for example, quaternary ammonium salts or special polymers, usually in the form of a rinse. Depending on the formulation, this treatment improves the combability, hold and fullness of hair and reduces split ends.

Likewise, functional cosmetic products are also known in the state of the art. In particular, these include the so-called "2-in-1" shampoos which not only clean the hair but also condition it. Such products are very popular among consumers because they eliminate at least one step, for example, the conditioning, with a traditional hair rinse due to their product performance.

Likewise, products for altering the natural hair color also play an important role in hair cosmetics. A distinction is made between permanent, semi-permanent or temporary dye systems based on chemical and/or natural dyes. However, the hair colors produced artificially by permanent, semi-permanent or temporary dye systems have the disadvantage that they can change in an unwanted manner—for example, during or after shampooing the hair.

The term "unwanted change" is understood to refer to the fading or leaching as well as the loss of brilliance of the color of the hair achieved by the respective dyeing.

Environmental influences and/or effects of sunlight can further increase these changes. The use of divalent metal salts in hair dyes to improve the holdability and thus the fastness of the dyeing is known from EP 2438900 A1.

There is still a need to produce active ingredients or combinations of active ingredients for hair treatment agents having good care properties, which also improve the adhesion of dyes to the hair fibers and thus maintain the fastness of the artificially produced hair color, and there is a need to further develop the hair treatment agent in this regard.

BRIEF SUMMARY

Hair treatment agents and methods are provided herein. In an embodiment, a hair treatment agent includes:
a) propionic acid and/or salts of propionic acid. at least one fatty alcohol,
b) at least one cationic surfactant,
c) at least one divalent or trivalent metal salt,
d) at least one silver salt chosen from silver acetate, silver adipate, silver citrate, silver galactarate, silver gluconate, silver lactate, silver malate, silver mandelate, silver salicylate, silver succinate, silver sulfate, and/or silver tartrate, and
e) at least one organic acid chosen from from adipic acid, succinic acid, citric acid, acetic acid, galactaric acid, gluconic acid, hydroxysuccinic acid, mandelic acid, lactic acid, salicylic acid, sulfuric acid, and/or tartaric acid.

In another embodiment, a method for treating hair includes applying a hair treatment agent to dry or damp hair, wherein the hair treatment agent includes:
a) at least one fatty alcohol,
b) at least one cationic surfactant,
c) at least one divalent or trivalent metal salt,
d) at least one silver salt chosen from silver acetate, silver adipate, silver citrate, silver galactarate, silver gluconate, silver lactate, silver malate, silver mandelate, silver salicylate, silver succinate, silver sulfate, and/or silver tartrate, and
e) at least one organic acid chosen from from adipic acid, succinic acid, citric acid, acetic acid, galactaric acid, gluconic acid, hydroxysuccinic acid, mandelic acid, lactic acid, salicylic acid, sulfuric acid, and/or tartaric acid,
where the hair treatment is agent is left on the hair for a time period of about 30 to about 300 seconds, and the rinsed out.

DETAILED DESCRIPTION

The following detailed description is merely exemplary in nature and is not intended to limit the hair treatment agents and methods for treating hair. Furthermore, there is no intention to be bound by any theory presented in the preceding background or the following detailed description.

It has now been found that a combination of certain ingredients has a particularly positive effect on dyed hair and the hair follicle treated with these ingredients.

A first subject matter as contemplated herein comprises hair treatment agents containing
a) at least one fatty alcohol,
b) at least one cationic surfactant,
c) at least one divalent or trivalent metal salt,
d) at least one silver salt selected from silver acetate, silver adipate, silver citrate, silver galactarate, silver gluconate, silver lactate, silver malate, silver mandelate, silver salicylate, silver succinate, silver sulfate, silver tartrate,
e) at least one organic acid selected from adipic acid, succinic acid, citric acid, acetic acid, galactaric acid, gluconic acid, hydroxysuccinic acid, mandelic acid, lactic acid, salicylic acid, sulfuric acid, tartaric acid.

Hair treatment agents in the sense as contemplated herein include, for example, hair shampoos, hair conditioners, conditioning shampoos, hair sprays, hair rinses, hair tinctures, hair packs, hair care treatments, permanent wave fixing solutions, hair dye shampoos, hair dyes, hair setting agents, hair packs, hairstyling preparations, blow-dry lotions, foam stabilizers, hair gels, hair waxes or combinations thereof. In view of the fact that men in particular are often hesitant to use several different products and/or several application steps, such products that a man would use anyway are preferred.

Preferred agents are therefore shampoos, conditioning agents or hair tonics.

The hair treatment agents contain at least one fatty alcohol.

The fatty alcohols are aliphatic, long-chain, monovalent primary alcohols with hydrocarbon moieties having 6 to 30, preferably 6 to 22 carbon atoms. The hydrocarbon moieties may be saturated or mono- and/or polyunsaturated. Fatty alcohols that are preferred for use within the scope as contemplated herein are selected from 1-hexanol, 1-heptanol, 1-octanol, 1-decanol, 1-dodecano I (lauryl alcohol), 1-tetradecanol (myristyl alcohol), 1-hexadecanol (cetyl alcohol), 1-heptadecanol (margaryl alcohol), 1-octadecanol (stearyl alcohol), 1-eisosanol (arachidyl alcohol), 1-docosanol (behenyl alcohol), 1-tetracosanol (lignoceryl alcohol), 1-hexacosanol (ceryl alcohol), 1-octacosanol (montanyl alcohol), 1-triacontanol (melissyl alcohol), cis-9-hexadecen-1-ol (palmitoleyl alcohol), cis-9-octadecen-1-ol (oleyl alcohol), trans-9-octadecen-1-ol (elaidyl alcohol), cis-11-octadecen-1-ol, 6,9,12-octadecatrien-1-ol (γ-linolenyl alcohol) and mixtures thereof.

Hair treatment agents that are particularly preferred are characterized in that they contain—based on their weight—about 0.1 to about 20% by weight, preferably about 0.5 to about 15% by weight, more preferably about 1 to about 10% by weight and in particular about 2 to about 8% by weight fatty alcohol(s) of the formula (II)

$$H_3C-(CH_2)_k-CH_2-OH \qquad (II)$$

wherein k stands for integers from 4 to 28, preferably from 6 to 24, more preferably from 8 to 22 and in particular for 10, 12, 14, 16, 18 or 20.

Especially preferred hair treatment agents as contemplated herein contain—based on their weight—about 0.1 to about 20% by weight, preferably about 0.5 to about 15% by weight, more preferably about 1 to about 10% by weight and in particular about 2 to about 8% by weight alcohol(s) from the group of 1-dodecanol (lauryl alcohol), 1-hexadecanol (cetyl alcohol), 1-octadecanol (stearyl alcohol), 1-docosanol (behenyl alcohol) wherein the amounts are based on the total amount of the aforementioned fatty alcohols in the composition.

Most especially preferred hair treatment agents as contemplated herein contain—based on their weight—about 0.1 to about 20% by weight, preferably about 0.5 to about 15% by weight, more preferably about 1 to about 10% by weight and in particular about 2 to about 8% by weight alcohol(s) from the group of 1-hexadecanol (cetyl alcohol), 1-octadecanol (stearyl alcohol), wherein the amounts are based on the total amount of the aforementioned fatty alcohols in the composition.

The hair treatment agents contain at least one cationic surfactant.

The cationic surfactant(s) is (are) preferably selected from the group of quaternary ammonium compounds and/or amidoamines, wherein preferred cationic surfactant(s) is (are) selected from alkyl trimethylammonium chlorides, preferably with 10 to 18 carbon atoms in the alkyl radical and/or by dialkyl dimethylammonium chlorides, preferably with 10 to 18 carbon atoms in the alkyl radical and/or trialkyl methylammonium chlorides, preferably with 10 to 18 carbon atoms in the alkyl radical and/or cetyl trimethylammonium chloride and/or stearyl trimethylammonium chloride and/or behenyl trimethylammonium chloride and/or distearyl dimethylammonium chloride and/or lauryl dimethylammonium chloride and/or lauryl dimethylbenzylammonium chloride and/or tricetyl methylammonium chloride quaternium-27 and/or quaternium-83.

Hair treatment agents preferred as contemplated herein contain—based on their weight—about 0.05 to about 20% by weight, preferably about 0.1 to about 10% by weight, more preferably about 0.25 to about 8% by weight and in particular about 0.5 to about 7% by weight cationic surfactant(s).

Especially preferred cationic surfactants are selected from compounds of the following formula (I):

In which at most three R1 to R4 radicals, independently of one another, stand for a saturated or unsaturated, branched or unbranched alkyl group with one to four carbon atoms, at least one R1 to R4 radical stands for a saturated or unsaturated, branched or unbranched alkyl chain with 8 to 30 carbon atoms, and A denotes a physiologically tolerable organic or inorganic anion.

In preferred compounds according to formula (I), two or three of the radicals R1 to R4 stand for a methyl or ethyl group, one or two radials R1 to R4 stand for a saturated or unsaturated, branched or unbranched alkyl chain with 14 to 26 carbon atoms, and A stands for a halide ion, a sulfate ion of the general formula $RSO_3^-$ where R has the meaning of saturated or unsaturated alkyl radicals with 1 to 4 carbon atoms or stands for an anionic radical of an organic acid, such as maleic acid, fumaric acid, oxalic acid, tartaric acid, citric acid, lactic acid or acetic acid.

More preferred compounds of formula (III) are those in which three radicals R1 to R4 stand for a methyl group, one radical R1 to R4 stands for a cetyl, palmityl, stearyl, arachidyl or behenyl group and A stands for a chloride or a methosulfate ion.

The at least one compound according to formula (I) is especially preferably selected from cetyl trimethylammonium chloride, cetyl trimethylammonium methosulfate, behenyl trimethyl-ammonium chloride and/or behenyl trimethylammonium methosulfate. These compounds may be used individually or in combination in the agent as contemplated herein, wherein the total amount of the compounds of formula (I) in the agent is preferably max. about 10% by weight, and wherein the quantitative statement is based on the total weight of the agent as contemplated herein.

An agent as contemplated herein especially preferably contains behenyl trimethylammonium chloride as the cationic agent. Hair treatment agents as contemplated herein that are preferred here preferably contain—based on their weight—about 0.05 to about 20% by weight, preferably about 0.1 to about 10% by weight, more preferably about 0.25 to about 8% by weight and in particular about 0.5 to about 7% by weight behenyl trimethylammonium chloride.

The hair treatment agents may also contain at least one ester quat as the cationic surfactant. "Ester quats" in the sense as contemplated herein are preferably understood to be compounds of the following formula (IV)

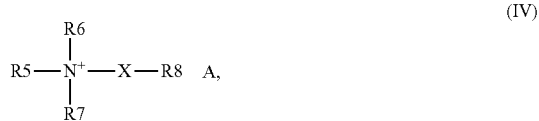

in which the R5, R6 and R7 radicals, independently of one another, may be the same or different and have the following meanings:
  a saturated or unsaturated, branched or unbranched alkyl radical with 1 to 4 carbon atoms, which may contain at least one hydroxyl group, or
  a saturated or unsaturated, branched or unbranched or cyclic saturated or unsaturated alkyl radical with 6 to 30 carbon atoms, which may contain at least one hydroxyl group or
  an aryl or alkylaryl radical, for example, phenyl or benzyl or
  (—X—R8) with the provision that at most two of the radicals R5, R6 or R7 may stand for (—X—R8), wherein
X has the following meaning:
  —$(CH_2)n$-, where n=1 to 20, preferably n=1 to 10 and especially preferably n=1 to 5, or
  —$(CH_2—CHR9-O)_n$, where n=1 to 200, preferably 1 to 100, more preferably 1 to 50 and especially preferably 1 to 20 as well as with R9 in the meaning of hydrogen, methyl or ethyl or
  a hydroxyalkylene group with 1 to 4 carbon atoms, which may be branched or unbranched, and contains at least one and at most three hydroxyl groups, and wherein
R8 has the following meaning:
  R10-O—CO—, where R10 is a saturated or unsaturated, branched or unbranched or cyclic, saturated or unsaturated alkyl radical with 6 to 30 carbon atoms, which may contain at least one hydroxyl group and which may optionally also be ethoxylated with 1 to 100 ethylene oxide units and/or 1 to 100 propylene oxide units or
  R11-CO—, where R11 is a saturated or unsaturated, branched or unbranched or cyclic, saturated or unsaturated alkyl radical with 6 to 30 carbon atoms, which may contain at least one hydroxyl group and which may optionally also be ethoxylated with 1 to 100 ethylene oxide units and/or 1 to 100 propylene oxide units, and
in which A stands for a physiologically tolerable organic or inorganic anion, preferably one of the radicals R5, R6 or R7 standing for the group (—X—R8), where R8 stands for a non-ethoxylated fatty acid radical such as for a palmitic, stearic, arachic or a behenic acid radical, in particular a stearic acid radical, and A stands for a halide ion, a sulfate ion of the general formula $RSO_3^-$ wherein R has the meaning of saturated or unsaturated alkyl radicals with 1 to 4 carbon atoms, or stands for an anionic radical of an organic acid, such as maleic acid, fumaric acid, oxalic acid, tartaric acid, citric acid, lactic acid or acetic acid, in particular for a chloride or a methosulfate ion.

The ester quats suitable for the agents as contemplated herein are preferably selected from at least one of the products distributed under the brand names Rewoquat®, Stepantex®, Dehyquart®, Armocare® and Akypoquat®, Specific examples of ester quats that are especially suitable as contemplated herein include the products Armocare® VGH-70, Dehyquart® F-75, Dehyquart® C-4046, Dehyquart® L80, Dehyquart® F-30, Dehyquart® AU-35, Rewoquat® WE18, Rewoquat® We38 DPG, Stepantex® VS 90 and Akypoquat® 131.

Agents as contemplated herein that are especially preferred as contemplated herein contain at least one of the compounds known by the INCI designations distearoylethyl hydroxyethylmonium methosulfate and distearoylethyl hydroxyethylmonium chloride as the ester quat.

Distearoylethyl hydroxyethylmonium methosulfate is especially preferred and may be present in the agents as contemplated herein in a preferred amount of about 0.1 to about 10% by weight, more preferably of about 0.5 to about 8% by weight, especially preferably of about 0.75 to about 6% by weight and in particular of about 1 to about 5% by weight, wherein the quantitative amounts are based on the total weight of the agent as contemplated herein.

The ester quat(s) may be added to the agents as contemplated herein either individually or in mixture with other care ingredients.

Because of the better handlability and processability, it may be advantageous if the ester quat(s)—in particular distearoylethyl hydroxyethylmonium methosulfate—is (are) added to the agents as contemplated herein as an active ingredient mixture. A particularly suitable example of such an active ingredient mixture is available, for example, under the brand name Dehyquart® F 75 from BASF (distearoylethyl hydroxyethylmonium methosulfate and cetearyl alcohol).

The hair treatment agents contain at least one divalent or trivalent metal salt. To achieve an optimum effect, it is advantageous if the metal salts are present in dissolved form in the agents as contemplated herein. In a preferred embodiment, the hair cleaning and hair care agents as contemplated herein therefore contain water-soluble divalent or trivalent metal salts. The term "water-soluble" here is understood to mean that at least 1 g of the respective salt can be dissolved complete in 1 liter of water at 20° C.

Suitable divalent or trivalent metal salts may be selected from divalent or trivalent organic and/or inorganic salts.

Particularly suitable cations within these salts can preferably be selected from alkaline earth metal cations as well as copper, zinc, iron(II), iron(III) and/or aluminum cations.

Alkaline earth metal cations are most especially preferred and calcium and magnesium cations are especially preferred. Especially suitable organic anions within these salts can preferably be selected from acetate, lactate, succinate, citrate, tartrate, malate, maleate, oxalate and/or glycolate ions. Most especially preferred are acetate, lactate and/or citrate salts with the cations mentioned above.

In particular, preferred organic salts include calcium lactate, calcium citrate, calcium acetate, magnesium lactate, magnesium citrate and/or magnesium acetate.

Especially suitable inorganic anions within these salts may be selected from halide, sulfate, phosphate and/or carbonate ions. Most especially preferred are sulfate and/or halide ions such as chloride and bromide ions.

In particular, preferred inorganic salts include calcium chloride, calcium sulfate, magnesium chloride and/or magnesium sulfate.

The amount by weight of the at least one divalent or trivalent metal salt in the total weight of the hair treatment agent as contemplated herein is preferably about 0.01 to about 10% by weight, preferably about 0.1 to about 7.5% by weight, more preferably about 0.2 to about 5% by weight and in particular about 0.3 to about 3% by weight.

Hair treatment agents preferred as contemplated herein contain—based on their weight—about 0.01 to about 10% by weight, preferably about 0.1 to about 7.5% by weight, more preferably about 0.2 to about 5% by weight and in particular about 0.3 to about 3% by weight of at least one divalent or trivalent metal salt from the group of organic or inorganic copper, zinc, iron(II), calcium, magnesium, iron (III) and/or aluminum salts.

Within this embodiment, the water-soluble salts are particularly preferred. Most especially preferred within this embodiment are calcium lactate, calcium citrate, calcium acetate, magnesium lactate, magnesium citrate, magnesium acetate, calcium halides, calcium hydroxide, magnesium halide and/or magnesium hydroxide.

The hair treatment agents contain at least one silver salt selected from silver acetate, silver adipate, silver citrate, silver galactarate, silver gluconate, silver lactate, silver malate, silver mandelate, silver salicylate, silver succinate, silver sulfate, silver tartrate or mixtures thereof.

Regardless of which silver salt(s) is (are) contained in the agents as contemplated herein, the preferred hair treatment agents as contemplated herein are those which contain—based on their weight—about 0.01 to about 2% by weight, preferably about 0.01 to about 1% by weight, more preferably about 0.025 to about 0.25% by weight and in particular about 0.05 to about 0.3% by weight silver salt(s).

The amount of the silver salt and/or silver salts selected is/are especially preferably selected, so that the compositions as contemplated herein have a defined silver ion content. The preferred hair treatment agents as contemplated herein here are those which contain silver ions in a total amount of 1-100 ppm, preferably 2-50 ppm, especially preferably 5-20 ppm, extraordinarily preferably 7-10 ppm, each based on the weight of the hair treatment agent.

The hair treatment agents contain at least one organic acid selected from adipic acid, succinic acid, citric acid, acetic acid, galactaric acid, gluconic acid, hydroxysuccinic acid, mandelic acid, lactic acid, salicylic acid, sulfuric acid, tartaric acid. Regardless of which acid(s) is (are) contained in the agents as contemplated herein, the preferred hair treatment agents as contemplated herein are those which contain—based on their weight—about 0.01 to about 3% by weight, preferably about 0.01 to about 2% by weight, more preferably about 0.025 to about 1.5% by weight and in particular about 0.05 to about 1% by weight organic acid(s) from the group of adipic acid, succinic acid, citric acid, acetic acid, galactaric acid, gluconic acid, hydroxysuccinic acid, mandelic acid, lactic acid, salicylic acid, sulfuric acid, tartaric acid.

It is extraordinarily preferred as contemplated herein when the acid contained in the agents and the silver salt contained in the agents are coordinated with one another, i.e., the silver salt of the respective acid being used is used.

Especially preferred agents as contemplated herein thus contain—based on their weight—about 0.01 to about 2% by weight, preferably about 0.01 to about 1% by weight, more preferably about 0.025 to about 0.25% by weight and in particular about 0.05 to about 0.3% by weight silver acetate and about 0.01 to about 3% by weight, preferably about 0.01 to about 2% by weight, more preferably about 0.025 to about 1.5% by weight and in particular about 0.05 to about 1% by weight acetic acid.

Additional particularly preferred agents as contemplated herein contain—based on their weight—about 0.01 to about 2% by weight, preferably about 0.01 to about 1% by weight, more preferably about 0.025 to about 0.25% by weight and in particular about 0.05 to about 0.3% by weight silver adipate and about 0.01 to about 3% by weight, preferably about 0.01 to about 2% by weight, more preferably about 0.025 to about 1.5% by weight and in particular about 0.05 to about 1% by weight adipic acid.

Additional particularly preferred agents as contemplated herein contain—based on their weight—about 0.01 to about 2% by weight, preferably about 0.01 to about 1% by weight, more preferably about 0.025 to about 0.25% by weight and in particular about 0.05 to about 0.3% by weight silver citrate and about 0.01 to about 3% by weight, preferably about 0.01 to about 2% by weight, more preferably about 0.025 to about 1.5% by weight and in particular about 0.05 to about 1% by weight citric acid.

Additional particularly preferred agents as contemplated herein contain—based on their weight—about 0.01 to about 2% by weight, preferably about 0.01 to about 1% by weight, more preferably about 0.025 to about 0.25% by weight and in particular about 0.05 to about 0.3% by weight silver galactarate and about 0.01 to about 3% by weight, preferably about 0.01 to about 2% by weight, more preferably about 0.025 to about 1.5% by weight and in particular about 0.05 to about 1% by weight galactaric acid.

Additional particularly preferred agents as contemplated herein contain—based on their weight—about 0.01 to about 2% by weight, preferably about 0.01 to about 1% by weight, more preferably about 0.025 to about 0.25% by weight and in particular about 0.05 to about 0.3% by weight silver gluconate, silver lactate, silver malate, silver mandelate, silver salicylate, silver succinate, silver sulfate, silver tartrate and 0.01 about to about 3% by weight, preferably about 0.01 to about 2% by weight, more preferably about 0.025 to about 1.5% by weight and in particular about 0.05 to about 1% by weight succinic acid, gluconic acid, hydroxysuccinic acid, mandelic acid, lactic acid, salicylic acid, sulfuric acid, tartaric acid.

Additional particularly preferred agents as contemplated herein contain—based on their weight—about 0.01 to about 2% by weight, preferably about 0.01 to about 1% by weight, more preferably about 0.025 to about 0.25% by weight and in particular about 0.05 to about 0.3% by weight silver gluconate and about 0.01 to about 3% by weight, preferably about 0.01 to about 2% by weight, more preferably about 0.025 to about 1.5% by weight and in particular about 0.05 to about 1% by weight gluconic acid.

Additional particularly preferred agents as contemplated herein contain—based on their weight—about 0.01 to about 2% by weight, preferably about 0.01 to about 1% by weight, more preferably about 0.025 to about 0.25% by weight and in particular about 0.05 to about 0.3% by weight silver lactate and about 0.01 to about 3% by weight, preferably about 0.01 to about 2% by weight, more preferably about 0.025 to about 1.5% by weight and in particular about 0.05 to about 1% by weight lactic acid.

Additional particularly preferred agents as contemplated herein contain—based on their weight—about 0.01 to about 2% by weight, preferably about 0.01 to about 1% by weight, more preferably about 0.025 to about 0.25% by weight and in particular about 0.05 to about 0.3% by weight silver malate and about 0.01 to about 3% by weight, preferably about 0.01 to about 2% by weight, more preferably about 0.025 to about 1.5% by weight and in particular about 0.05 to about 1% by weight hydroxysuccinic acid.

Additional particularly preferred agents as contemplated herein contain—based on their weight—about 0.01 to about 2% by weight, preferably about 0.01 to about 1% by weight, more preferably about 0.025 to about 0.25% by weight and in particular about 0.05 to about 0.3% by weight silver mandelate and about 0.01 to about 3% by weight, preferably about 0.01 to about 2% by weight, more preferably about 0.025 to about 1.5% by weight and in particular about 0.05 to about 1% by weight mandelic acid.

Additional particularly preferred agents as contemplated herein contain—based on their weight—about 0.01 to about 2% by weight, preferably about 0.01 to about 1% by weight, more preferably about 0.025 to about 0.25% by weight and in particular about 0.05 to about 0.3% by weight silver salicylate and about 0.01 to about 3% by weight, preferably about 0.01 to about 2% by weight, more preferably about 0.025 to about 1.5% by weight and in particular about 0.05 to about 1% by weight salicylic acid.

Additional particularly preferred agents as contemplated herein contain—based on their weight—about 0.01 to about 2% by weight, preferably about 0.01 to about 1% by weight, more preferably about 0.025 to about 0.25% by weight and in particular about 0.05 to about 0.3% by weight silver succinate and about 0.01 to about 3% by weight, preferably about 0.01 to about 2% by weight, more preferably about 0.025 to about 1.5% by weight and in particular about 0.05 to about 1% by weight succinic acid.

Additional particularly preferred agents as contemplated herein contain—based on their weight—about 0.01 to about 2% by weight, preferably about 0.01 to about 1% by weight, more preferably about 0.025 to about 0.25% by weight and in particular about 0.05 to about 0.3% by weight silver sulfate and about 0.01 to about 3% by weight, preferably about 0.01 to about 2% by weight, more preferably about 0.025 to about 1.5% by weight and in particular about 0.05 to about 1% by weight sulfuric acid.

Additional particularly preferred agents as contemplated herein contain—based on their weight—about 0.01 to about 2% by weight, preferably about 0.01 to about 1% by weight, more preferably about 0.025 to about 0.25% by weight and in particular about 0.05 to about 0.3% by weight silver tartrate and about 0.01 to about 3% by weight, preferably about 0.01 to about 2% by weight, more preferably about 0.025 to about 1.5% by weight and in particular about 0.05 to about 1% by weight tartaric acid.

It has proven advantageous in particular for the two ingredients, the silver salt and the corresponding acid, to be used in a prefabricated form in the form of a complex. Such complexes can worked up with suitable passivating agents to form a separate raw material that is stable in storage and can be incorporated then in a stable form even into highly aqueous systems.

Hair treatment agents preferred as contemplated herein contain—based on their weight—about 0.01 to about 5% by weight, preferably about 0.01 to about 3% by weight, more preferably about 0.025 to about 1.5% by weight and in particular about 0.05 to about 1% by weight silver lactate-lactic acid complexes of the form

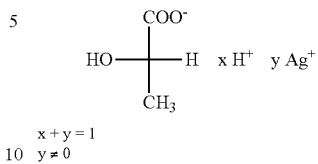

$x + y = 1$
$y \neq 0$ or of the form

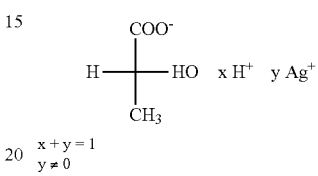

$x + y = 1$
$y \neq 0$ or with a water content of up to about 90% by weight, based on the total mass of the complex in combination with one or more passivating agents selected from the group of sheet silicates and/or talc.

Further preferred hair treatment agents contain—based on the weight—about 0.01 to about 5% by weight, preferably about 0.01 to about 3% by weight, more preferably about 0.025 to about 1.5% by weight and in particular about 0.05 to about 1% by weight silver acetate-acetic acid complexes of the form

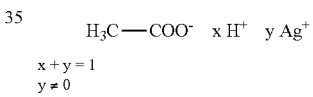

$x + y = 1$
$y \neq 0$ with a water content of up to 90% by weight, based on the total mass of the complex in combination with one or more passivating agents selected from the group of sheet silicates and/or talc.

Further preferred hair treatment agents contain—based on their weight—about 0.01 to about 5% by weight, preferably about 0.01 to about 3% by weight, more preferably about 0.025 to about 1.5% by weight and in particular about 0.05 to about 1% by weight silver sulfate-sulfuric acid complexes of the form

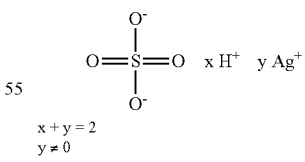

$x + y = 2$
$y \neq 0$ with a water content of up to about 90% by weight, based on the total mass of the complex in combination with one or more passivating agents selected from the group of sheet silicates and/or talc.

Further preferred hair treatment agents contain—based on their weight—about 0.01 to about 5% by weight, preferably about 0.01 to about 3% by weight, more preferably about 0.025 to about 1.5% by weight and in particular about 0.05 to about 1% by weight silver malate-hydroxysuccinic acid complexes of the form

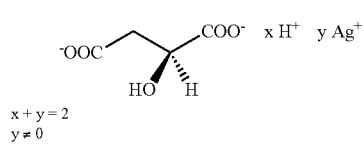

x + y = 2
y ≠ 0 or of the form

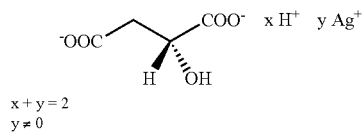

x + y = 2
y ≠ 0 with a water content of up to about 90% by weight, based on the total mass of the complex, in combination with one or more passivating agents selected from the group of sheet silicates and/or talc.

Further preferred hair treatment agents contain—based on their weight—about 0.01 to about 5% by weight, preferably about 0.01 to about 3% by weight, more preferably about 0.025 to about 1.5% by weight and in particular about 0.05 to about 1% by weight silver succinate-succinic acid complexes of the form

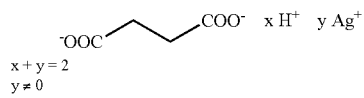

x + y = 2
y ≠ 0 with a water content of up to 90% by weight, based on the total mass of the complex in combination with one or more passivating agents selected from the group of sheet silicates and/or talc.

Further preferred hair treatment agents contain—based on their weight—about 0.01 to about 5% by weight, preferably about 0.01 to about 3% by weight, more preferably about 0.025 to about 1.5% by weight and in particular about 0.05 to about 1% by weight silver tartrate-tartaric acid complexes of the form

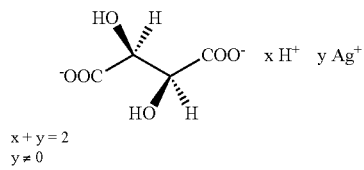

x + y = 2
y ≠ 0 or of the form

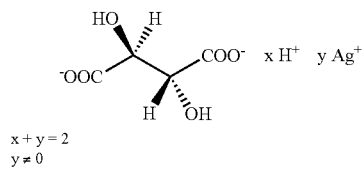

x + y = 2
y ≠ 0 or of the form

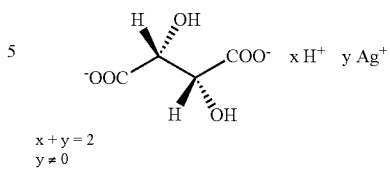

x + y = 2
y ≠ 0 with a water content of up to about 90% by weight, based on the total mass of the complex in combination with one or more passivating agents selected from the group of sheet silicates and/or talc.

Further preferred hair treatment agents contain—based on their weight—about 0.01 to about 5% by weight, preferably about 0.01 to about 3% by weight, more preferably about 0.025 to about 1.5% by weight and in particular about 0.05 to about 1% by weight silver mandelate-mandelic acid complexes of the form

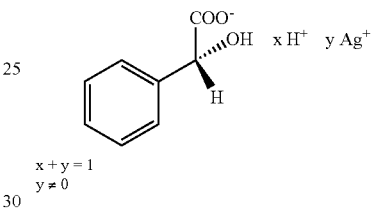

x + y = 1
y ≠ 0 or of the form

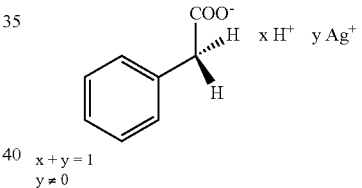

x + y = 1
y ≠ 0 with a water content of up to about 90% by weight, based on the total mass of the complex in combination with one or more passivating agents selected from the group of sheet silicates and/or talc.

Further preferred hair treatment agents contain—based on their weight—about 0.01 to about 5% by weight, preferably about 0.01 to about 3% by weight, more preferably about 0.025 to about 1.5% by weight and in particular about 0.05 to about 1% by weight silver salicylate-salicylic acid complexes of the form

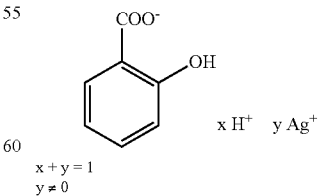

x + y = 1
y ≠ 0 with a water content of up to about 90% by weight, based on the total mass of the complex in combination with one or more passivating agents selected from the group of sheet silicates and/or talc.

Further preferred hair treatment agents contain—based on their weight—about 0.01 to about 5% by weight, preferably about 0.01 to about 3% by weight, more preferably about 0.025 to about 1.5% by weight and in particular about 0.05 to about 1% by weight silver gluconate-gluconic acid complexes of the form

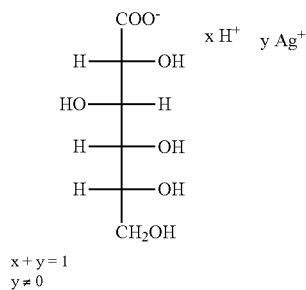

x + y = 1
y ≠ 0 with a water content of up to about 90% by weight, based on the total mass of the complex in combination with one or more passivating agents selected from the group of sheet silicates and/or talc.

Particularly preferred hair treatment agents contain—based on their weight—about 0.01 to about 2% by weight, preferably about 0.01 to about 1% by weight, more preferably about 0.025 to about 0.25% by weight and in particular about 0.05 to about 0.3% by weight silver citrate-citric acid complexes of the form

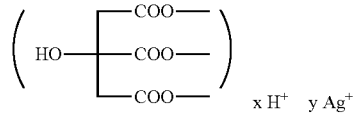

where x+y=3 and y≠0
with a water content of up to about 90% by weight, based on the total mass of the complex, in combination with one or more passivating agents selected from the group of silicic acids.

Further preferred hair treatment agents contain—based on their weight—about 0.01 to about 5% by weight, preferably about 0.01 to about 3% by weight, more preferably about 0.025 to about 1.5% by weight and in particular about 0.05 to about 1% by weight silver galactarate-galactaric acid complexes of the form

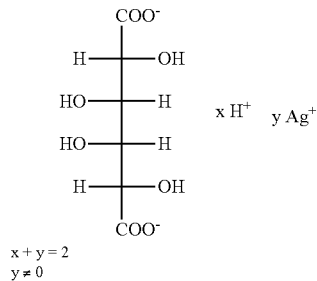

x + y = 2
y ≠ 0 with a water content of up to about 90% by weight, based on the total mass of the complex in combination with one or more passivating agents selected from the group of sheet silicates and/or talc.

The hair treatment agents preferably contain the active ingredients described above in a cosmetically acceptable vehicle. Within the scope as contemplated herein, this is preferably understood to be an aqueous or aqueous alcoholic vehicle.

The cosmetic vehicle preferably contains at least about 50% by weight, more preferably at least about 60% by weight, especially preferably at least about 70% by weight and in particular preferably at least 75% by weight water.

In addition, the cosmetic vehicle may preferably contain about 0.01 to about 40% by weight, preferably about 0.05 to about 30% by weight and in particular about 0.1 to about 20% by weight of at least one alcohol.

Suitable alcohols include, for example, ethanol, ethyl diglycol, 1-propanol, 2-propanol, isopropanol, 1,2-propylene glycol, glycerol, diglycerol, triglycerol, 1-butanol, 2-butanol, 1,2-butandiol, 1,3-Butandiol, 1-pentanol, 2-pentanol, 1,2-pentandiol, 1,5-pentandiol, 1-hexanol, 2-hexanol, 1,2-hexanediol, 1,6-hexanediol, polyethylene glycols, sorbitol, sorbitan, benzyl alcohol or mixtures of these alcohols.

These water-soluble alcohols are particularly preferred. Preferred in particular are ethanol, 1,2-propylene glycol, glycerin, benzyl alcohol and mixtures of these alcohols.

For a very good scalp/skin tolerability of the hair treatment agents as contemplated herein, it is advantageous if they have a slightly acidic pH.

It has been found that the agents as contemplated herein have a particularly good skin tolerability and mildness in a pH range from 4.2 to 5.8.

In a first preferred embodiment, the hair treatment agents as contemplated herein therefore preferably have a pH in the range of 4.2 to 5.8, more preferably from 4.25 to 5.6, especially preferably from 4.3 to 5.5, extraordinarily preferably from 4.35 to 5.4 and in particular preferably from 4.4 to 5.3.

The hair treatment agents as contemplated herein may contain silicone(s).

Agents preferred as contemplated herein are characterized in that they contain at least one silicone selected from:
(i) Polyalkyl siloxanes, polyaryl siloxanes, polyalkylaryl siloxanes which are volatile or nonvolatile, linear, branched or cyclic, crosslinked or not crosslinked;
(ii) Polysiloxanes containing in their general structure one or more organofunctional groups selected from:
  a) substituted or unsubstituted aminated groups;
  b) perfluorinated groups;
  c) thiol groups;
  d) carboxylate groups;
  e) hydroxylated groups;
  f) alkoxylated groups;
  g) acyloxyalkyl groups;
  h) amphoteric groups;
  i) bisulfite groups;
  j) hydroxyacylamino groups;
  k) carboxyl groups;
  l) sulfonic acid groups; and
  m) sulfate or thiosulfate groups;
(iii) Linear polysiloxane (A)-polyoxyalkylene (B)-block copolymers of (A-B). type, where n>3;
(iv) Grafted silicone polymers with a non-silicon-containing organic backbone structure, consisting of an organic main chain formed from organic monomers, which do not contain any silicone and onto which at least one polysiloxane macromer has been grafted in the chain and optionally on at least one chain terminus;
(v) Grafted silicone polymers with polysiloxane backbone structure, onto which non-silicone-containing organic monomers have been grafted, having a polysiloxane main chain onto which at least one organic macromer containing no silicone has been grafted in the chain as well as optionally onto at least one of its termini or mixtures thereof.

Hair treatment agents preferred as contemplated herein are characterized in that they contain—based on their weight—about 0.01 to about 20% by weight, preferably about 0.1 to about 10% by weight, more preferably about 0.5 to about 7.5% by weight and in particular about 1 to about 5% by weight silicone(s).

Preferred silicones are described below.

Particularly preferred agents as contemplated herein are characterized in that they contain at least one silicone of the formula Si—I:

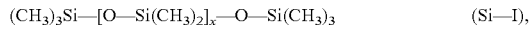

$$(CH_3)_3Si-[O-Si(CH_3)_2]_x-O-Si(CH_3)_3 \quad (Si-I),$$

where x stands for a number from 0 to 100, preferably from 0 to 50, more preferably from 0 to 20 and in particular from 0 to 10.

According to the INCI nomenclature, these silicones are referred to as dimethicone. The following compounds are preferably used as the silicone of the formula Si—I within the scope as contemplated herein:

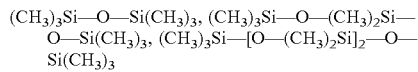

(CH$_3$)$_3$Si—O—Si(CH$_3$)$_3$, (CH$_3$)$_3$Si—O—(CH$_3$)$_2$Si—O—Si(CH$_3$)$_3$, (CH$_3$)$_3$Si—[O—(CH$_3$)$_2$Si]$_2$—O—Si(CH$_3$)$_3$

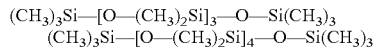

(CH$_3$)$_3$Si—[O—(CH$_3$)$_2$Si]$_3$—O—Si(CH$_3$)$_3$
(CH$_3$)$_3$Si—[O—(CH$_3$)$_2$Si]$_4$—O—Si(CH$_3$)$_3$

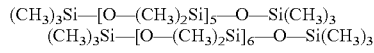

(CH$_3$)$_3$Si—[O—(CH$_3$)$_2$Si]$_5$—O—Si(CH$_3$)$_3$
(CH$_3$)$_3$Si—[O—(CH$_3$)$_2$Si]$_6$—O—Si(CH$_3$)$_3$

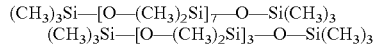

(CH$_3$)$_3$Si—[O—(CH$_3$)$_2$Si]$_7$—O—Si(CH$_3$)$_3$
(CH$_3$)$_3$Si—[O—(CH$_3$)$_2$Si]$_8$—O—Si(CH$_3$)$_3$

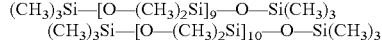

(CH$_3$)$_3$Si—[O—(CH$_3$)$_2$Si]$_9$—O—Si(CH$_3$)$_3$
(CH$_3$)$_3$Si—[O—(CH$_3$)$_2$Si]$_{10}$—O—Si(CH$_3$)$_3$

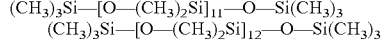

(CH$_3$)$_3$Si—[O—(CH$_3$)$_2$Si]$_{11}$—O—Si(CH$_3$)$_3$
(CH$_3$)$_3$Si—[O—(CH$_3$)$_2$Si]$_{12}$—O—Si(CH$_3$)$_3$

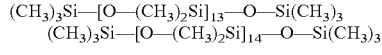

(CH$_3$)$_3$Si—[O—(CH$_3$)$_2$Si]$_{13}$—O—Si(CH$_3$)$_3$
(CH$_3$)$_3$Si—[O—(CH$_3$)$_2$Si]$_{14}$—O—Si(CH$_3$)$_3$

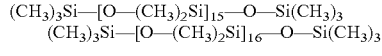

(CH$_3$)$_3$Si—[O—(CH$_3$)$_2$Si]$_{15}$—O—Si(CH$_3$)$_3$
(CH$_3$)$_3$Si—[O—(CH$_3$)$_2$Si]$_{16}$—O—Si(CH$_3$)$_3$

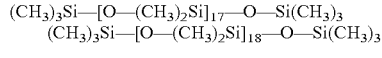

(CH$_3$)$_3$Si—[O—(CH$_3$)$_2$Si]$_{17}$—O—Si(CH$_3$)$_3$
(CH$_3$)$_3$Si—[O—(CH$_3$)$_2$Si]$_{18}$—O—Si(CH$_3$)$_3$

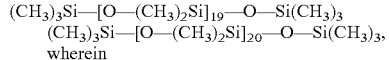

(CH$_3$)$_3$Si—[O—(CH$_3$)$_2$Si]$_{19}$—O—Si(CH$_3$)$_3$
(CH$_3$)$_3$Si—[O—(CH$_3$)$_2$Si]$_{20}$—O—Si(CH$_3$)$_3$, wherein

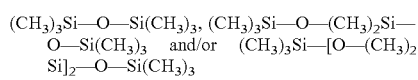

(CH$_3$)$_3$Si—O—Si(CH$_3$)$_3$, (CH$_3$)$_3$Si—O—(CH$_3$)$_2$Si—O—Si(CH$_3$)$_3$ and/or (CH$_3$)$_3$Si—[O—(CH$_3$)$_2$Si]$_2$—O—Si(CH$_3$)$_3$ are especially preferred.

Mixtures of the aforementioned silicones may of course also be present in the agents as contemplated herein. Preferred silicones that can be used as contemplated herein and have a viscosity of 0.2 to 2 mm$^2$s$^{-1}$ at 20° C., wherein silicones with a viscosity of 0.5 to 1 mm$^2$s$^{-1}$ are especially preferred.

Especially preferred agents as contemplated herein contain one or more amino-functional silicones. Such silicones can be described by the formula:

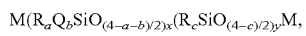

$$M(R_aQ_bSiO_{(4-a-b)/2})_x(R_cSiO_{(4-c)/2})_yM,$$

where R in the above formula stands for a hydrocarbon or a hydrocarbon moiety with 1 to approx. 6 carbon atoms, Q is a polar radical of the general formula —R$^1$HZ, where R$^1$ is a divalent connecting group that is bound to hydrogen and the Z radical, comprised of carbon and hydrogen atoms, carbon, hydrogen and oxygen atoms, or carbon, hydrogen and nitrogen atoms, and Z is an organic amino-functional radical containing at least one amino-functional group; "a" assumes values in the range from approx. 0 to approx. 2, "b" assumes values in the range from approx. 1 to approx. 3, "a"+"b" is less than or equal to 3, and "c" is a number in the range from approx. 1 to approx. 3, and x is a number in the range from 1 to approx. 2000, preferably from approx. 3 to approx. 50, and most preferably from approx. 3 to approx. 25, and y is a number in the range from approx. 20 to approx. 10,000, preferably from approx. 125 to approx. 10,000, and most preferably from approx. 150 to approx. 1000, and M is a suitable terminal silicone group, such as those known in the state of the art, preferably trimethylsiloxy. Non-restrictive examples of the radicals represented by R include alkyl radicals such as methyl, ethyl, propyl, isopropyl, butyl, isobutyl, amyl, isoamyl, hexyl, isohexyl and the like; alkenyl radicals such as vinyl, halovinyl, alkyl vinyl, allyl, haloallyl, alkyl allyl; cycloalkyl radicals, such as cyclobutyl, cyclopentyl, cyclohexyl and the like; phenyl radicals, benzyl radicals, halohydrocarbon radicals such as 3-chloropropyl, 4-bromobutyl, 3,3,3-trifluoropropyl, chlorocyclohexyl, bromophenyl, chlorophenyl and the like as well as sulfur-containing radicals, such as mercaptoethyl, mercaptopropyl, mercaptohexyl, mercaptophenyl and the like; R is preferably an alkyl radical containing 1 to approx. 6 carbon atoms, and R is most preferably methyl. Examples of R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$CC(O)OCH$_2$CH$_2$—, —C$_6$H$_4$C$_6$H$_4$—, —C$_6$H$_4$CH$_2$C$_6$H$_4$— and —(CH$_2$)$_3$C(O)SCH$_2$CH$_2$—.

Z is an organic amino-functional radical containing at least one functional amino group. One possible formula for Z is NH(CH$_2$)$_z$NH$_2$, where z is 1 or more. Another possible formula for Z is —NH(CH$_2$)$_z$(CH$_2$)$_{zz}$NH, where both z and zz, independently of one another, stand for 1 or more, and this structure includes diamino ring structures, such as piperazinyl. Z is most preferably an —NHCH$_2$CH$_2$NH$_2$ radical. Another possible formula for Z is —N(CH$_2$)$_z$(CH$_2$)$_{zz}$NX$_2$ or —NX$_2$, wherein each X of X$_2$ is selected independently from the group consisting of hydrogen and alkyl groups with 1 to 12 carbon atoms, and zz is 0.

Q is most preferably a polar amine-functional radical of the formula —CH$_2$CH$_2$CH$_2$NHCH$_2$CH$_2$NH$_2$. In these formulas "a" assumes values in the range from approx. 0 to approx. 2, "b" assumes values in the range from approx. 1 to approx. 3, "a"+"b" is less than or equal to 3 and "c" is a number in the range from approx. 1 to approx. 3. The molar ratio of the R$_a$Q$_b$SiO$_{(4-a-b)/2}$ units to the R$_c$SiO$_{(4-c)/2}$ units is in the range from approx. 1:2 to 1:65, preferably from approx. 1:5 to approx. 1:65 and most preferably from approx. 1:15 to approx. 1:20. If one or more silicones from the above formulas are used, then the various variable substituents in the above formula may be different with the various silicone components that are present in the silicone mixture.

Preferred agents as contemplated herein are characterized in that they contain an amino-functional silicone of the formula (Si-II):

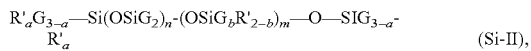 (Si-II), wherein
G is —H, a phenyl group, —OH, —O—CH$_3$, —CH$_3$, —O—CH$_2$CH$_3$, —CH$_2$CH$_3$, —O—CH$_2$CH$_2$CH$_3$, —CH$_2$CH$_2$CH$_3$, —O—CH(CH$_3$)$_2$, —CH(CH$_3$)$_2$, —O—CH$_2$CH$_2$CH$_2$CH$_3$, —CH$_2$CH$_2$CH$_2$CH$_3$, —O—CH$_2$CH(CH$_3$)$_2$, —CH$_2$CH(CH$_3$)$_2$, —O—CH(CH$_3$)CH$_2$CH$_3$, —CH(CH$_3$)CH$_2$CH$_3$, —O—C(CH$_3$)$_3$, —C(CH$_3$)$_3$, a stands for a number between 0 and 3, in particular 0,
b stands for a number between 0 and 1, in particular 1,
m and n are numbers the sum of which (m+n) is between 1 and 2000, preferably between 50 and 150, where n preferably assumes values from 0 to 1999 and in particular from 49 to 149 and m preferably assumes values from 1 to 2000, in particular from 1 to 10,
R' is a monovalent radical selected from
-Q-N(R")—CH$_2$—CH$_2$—N(R")$_2$
-Q-N(R")$_2$
-Q-N$^+$(R")$_3$A$^-$
-Q-N$^+$H(R")$_2$A$^-$
-Q-N$^+$H$_2$(R")A$^-$
-Q-N(R")—CH$_2$—CH$_2$—N$^+$R"H$_2$A$^-$,
where each Q stands for a chemical bond, —CH$_2$—, —CH$_2$—CH$_2$—, —CH$_2$CH$_2$CH$_2$—, —C(CH$_3$)$_2$—, —CH$_2$CH$_2$CH$_2$CH$_2$—, —CH$_2$C(CH$_3$)$_2$—, —CH(CH$_3$)CH$_2$CH$_2$—,
R" stands for the same or different radicals from the group —H, phenyl, benzyl, —CH$_2$—CH(CH$_3$)Ph, the C$_{1-20}$ alkyl radicals, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, and A represents an anion, which is preferably selected from chloride, bromide, iodide or methosulfate.

Especially preferred agents as contemplated herein are characterized in that they contain at least one amino-functional silicone of the formula (Si-IIa):

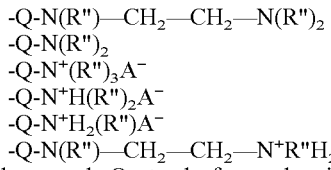 (Si-IIa)

where m and n are numbers the sum of which (m+n) is between 1 and 2000, preferably between 50 and 150, where n preferably assumes values from 0 to 1999 and in particular from 49 to 149, and m preferably assumes values from 1 to 2000, in particular from 1 to 10.

According to the INCI declaration, these silicones are referred to as trimethylsilyl-amodimethicone.

Agents as contemplated herein containing an amino-functional silicone of the formula (Si-IIb) are particularly preferred:

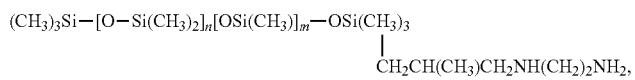

(Si-IIb)

where R stands for —OH, —O—CH$_3$ or a —CH$_3$ group and m, n1 and n2 are numbers the sum of which (m+n1+n2) is between 1 and 2000, preferably between 50 and 150, where the sum (n1+n2) preferably assumes values from 0 to 1999 and in particular from 49 to 149, and m preferably assumes values from 1 to 2000 in particular from 1 to 10.

According to the INCI declaration, these silicones are referred to as amodimethicone.

Regardless of which amino-functional silicones are used, agents as contemplated herein containing an amino-functional silicone whose amine number is greater than 0.25 meq/g, preferably greater than 0.3 meq/g and in particular greater than 0.4 meq/g are preferred. The amine number here stands for the milliequivalents of amine per gram of amino-functional silicone. It can be determined by titration and is also given in units of mg KOH/g.

Preferred agents as contemplated herein are characterized in that they contain, based on their weight, about 0.01 to about 20% by weight, preferably about 0.1 to about 10% by weight, especially preferably about 0.5 to about 7.5% by weight and in particular about 1 to about 5% by weight amino-functional silicone(s).

The agents as contemplated herein especially preferably contain amino-functional silicone(s) with terminal hydroxyl group(s). Some special amino-functional silicones with terminal hydroxyl groups have proven to be particularly suitable in the agents as contemplated herein and are described below.

Agents preferred as contemplated herein are characterized in that they contain, based on their weight, about 0.01 to about 20% by weight, preferably about 0.1 to about 10% by weight, especially preferably about 5 to about 7.5% by weight and in particular about 1 to about 5% by weight of at least one silicone of the following formula (Si-III):

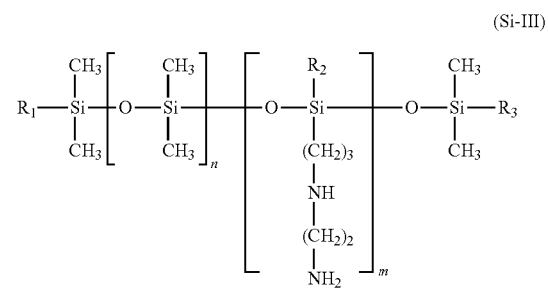

(Si-III)

in which
m and n denote numbers selected so that the sum (n+m) is in the range of 1 to 1000, n is a number in the range of 0 to 999 and m is a number in the range from 1 to 1000, R$_1$, R$_2$ and R$_3$, which may be the same or different, denote a hydroxyl group or a C$_{1-4}$ alkoxy group, wherein at least one of the R to R$_3$ groups denotes a hydroxyl group.

Additional agents preferred as contemplated herein are characterized in that they contain, based on their weight, about 0.01 to about 20% by weight, preferably about 0.1 to about 10% by weight, especially preferably about 0.5 to about 7.5% by weight and in particular about 1 to about 5% by weight of at least one silicone of the following formula (Si-IV):

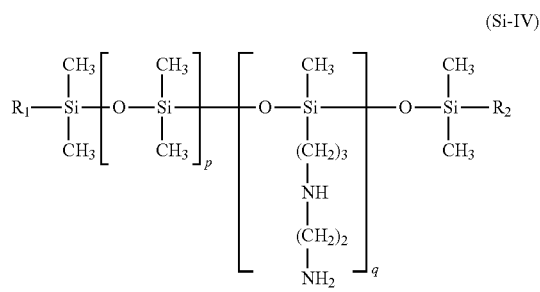
(Si-IV)

in which p and q denote numbers selected, so that their sum (p+q) is in the range of 1 to 1000, p is a number in the range from 0 to 999 and q is a number in the range from 1 to 1000, R$_1$ and R$_2$, which are different, denote a hydroxyl group or a C$_{1-4}$ alkoxy group, wherein at least one of the groups R to R$_2$ denotes a hydroxyl group.

The silicones of formula (Si-III) and (Si-IV) are different due to the grouping on the Si atom which carries the nitrogen-containing group. In formula (Si-III), R$_2$ denotes a hydroxyl group or a C$_{1-4}$ alkoxy group while the radical in formula (Si-IV) is a methyl group. The individual Si groups characterized with the indices m and n and/or p and q need not be present as blocks, but instead the individual units may also be present in a random distribution, i.e., in the formulas (Si-IIII) and (Si-IV), each R$_1$—Si(CH$_3$)$_2$ group is not necessarily bound to a —[O—SI(CH$_3$)$_2$] group.

In the method as contemplated herein, pretreatment agents containing at least one silicone of formula (Si-V) have proven to be particularly effective with respect to the desired effects:

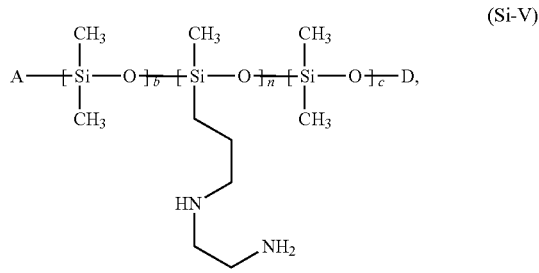
(Si-V)

where

A stands for a group —OH, —O—Si(CH$_3$)$_3$, —O—Si(CH$_3$)$_2$OH, —O—Si(CH$_3$)$_2$OCH$_3$, D stands for a group —H, —Si(CH$_3$)$_3$, —Si(CH$_3$)$_2$OH, —Si(CH$_3$)$_2$OCH$_3$, b, n and c stand for numbers between 0 and 1000, with the provisions that n>0 and b+c>0 at least one of the conditions A=—OH and/or D=—H is satisfied.

Preferred inventive agents as contemplated herein contain, based on their weight, about 0.01 to about 20% by weight, preferably about 0.1 to about 10% by weight, especially preferably about 0.5 to about 7.5% by weight and in particular about 1 to about 5% by weight of at least one silicone of formula (Si-V):

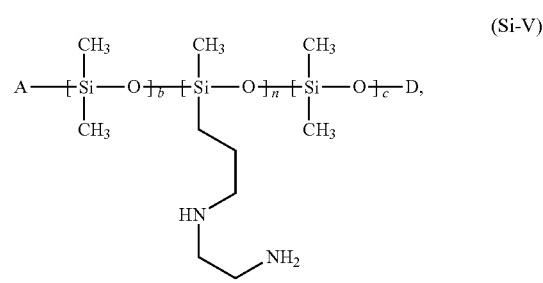
(Si-V)

where

A stands for a group —OH, —O—Si(CH$_3$)$_3$, —O—Si(CH$_3$)$_2$OH, —O—Si(CH$_3$)$_2$OCH$_3$, D stands for a group —H, —Si(CH$_3$)$_3$, —Si(CH$_3$)$_2$OH, —Si(CH$_3$)$_2$OCH$_3$, b, n and c stand for numbers between 0 and 1000, with the provisions:

n>0 and b+c>0 at least one of the conditions A=—OH and/or D=—H is satisfied.

In the formula (SiV) given above, the individual siloxane units with the indices b, c and n are randomly distributed, i.e., these need not necessarily be block copolymers.

Additional especially preferred silicones are 4-morpholinomethyl-substituted agents as contemplated herein, which contain, based on their weight, about 0.01 to about 20% by weight, preferably about 0.1 to about 10% by weight, especially preferably about 0.5 to about 7.5% by weight and in particular about 1 to about 5% by weight of at least one 4-morpholinomethyl-substituted silicone of the formula (Si-VI):

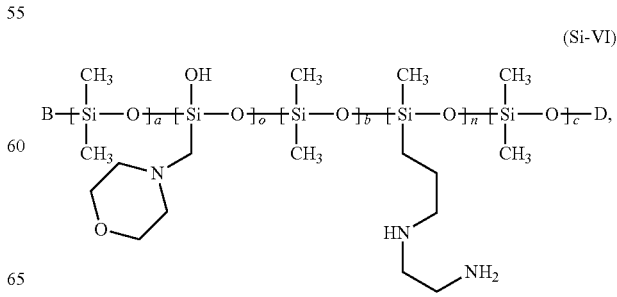
(Si-VI)

in which

A stands for a structural unit (i) bound by —O—

$$*-\left[\begin{array}{c}\text{CH}_3\\|\\\text{Si}-\text{O}\\|\\\text{CH}_3\end{array}\right]_m-* \qquad (i)$$

or an oligomeric or polymeric radical containing structural units of formula (i), bound by an —O—, or stands for —OH,
* stands for a bond to the structural (i) or for a terminal group B (Si-bound) or D (O-bound),
B stands for a group —OH, —O—Si(CH$_3$)$_3$, —O—Si(CH$_3$)$_2$OH, —O—Si(CH$_3$)$_2$OCH$_3$,
D stands for a group —H, —Si(CH$_3$)$_3$, —Si(CH$_3$)$_2$OH, —Si(CH$_3$)$_2$OCH$_3$,
a, b and c stand for numbers between 0 and 1000 with the provision that a+b+c>0,
m, n and o stand for numbers between 1 and 1000,
with the provision that at least one of the conditions B=—OH and D=—H is satisfied.

Structural formula (Si-VI) should illustrate that the siloxane groups n and o need not necessarily be bound directly to a terminal group B and/or D. Instead in preferred formulas (Si-VI) a>0 or b>0 and in especially preferred formulas (Si-VI) a>0 and b>0, i.e., the terminal group B and D is preferably bound to a dimethylsiloxy group. The silicones used as contemplated herein as represented by formula (Si-VI) may be trimethylsilyl-terminated (D or B=—Si(CH$_3$)$_3$) but they may also be terminated at both ends by dimethylsilylhydroxy or at one end by dimethylsilylhydroxy and dimethylsilylmethoxy. Within the scope as contemplated herein, silicones that are especially preferred for use are selected from silicones, in which B=—O—Si(CH$_3$)$_2$OH and D=—Si(CH$_3$)$_3$ B=—O—Si(CH$_3$)$_2$OH and D=—Si(CH$_3$)$_2$OH B=—O—Si(CH$_3$)$_2$OH and D=—Si(CH$_3$)$_2$OCH$_3$ B=—O—Si(CH$_3$)$_3$ and D=—Si(CH$_3$)$_2$OH B=—O—Si(CH$_3$)$_2$OCH$_3$ and D=—Si(CH$_3$)$_2$OH These silicones lead to exorbitant improvements in the hair properties of the hair treated with the agents as contemplated herein, in particular to a greatly improved protection under oxidative treatment.

The radical A in the formula (Si-VI) may stand for:
a structural unit (i) bound by an —O— or
an oligomeric or polymeric radical containing structural units of formula (i) bound by an —O— or —OH.

Thus formula (Si-VI) can be specified more precisely as one of the formulas (Si-Va), (Si-VIb) or (Si-Vic):

(Si-VIa)

(Si-VIb)

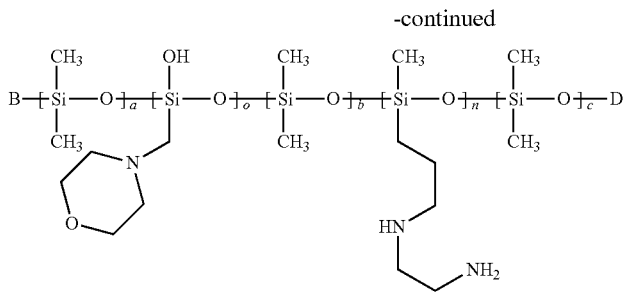
-continued

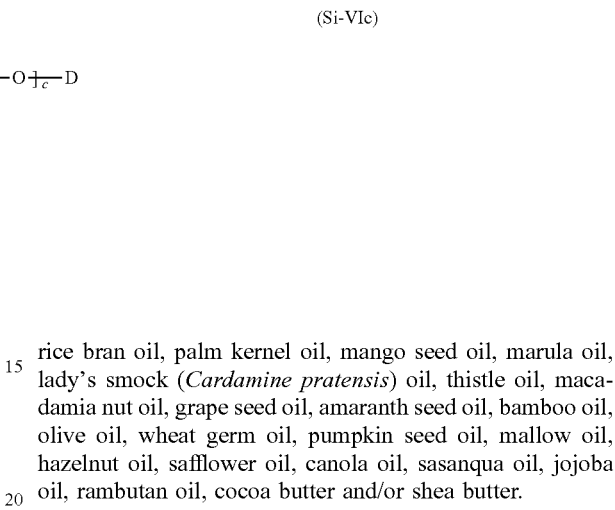
(Si-VIc)

Regardless of the type of amino-functional silicone(s) with terminal hydroxyl group(s), the agents as contemplated herein contain the silicone(s) preferably in the form of an emulsion, especially preferably in the form of a microemulsion. It has been found that the effect of the silicones used in the agents as contemplated herein can be further increased if certain nonionic components are also used in the agents. Furthermore, these nonionic components have positive effects on the storage stability of the agents. Nonionic components that are particularly suitable here include ethoxylates of decanol, undecanol, dodecanol, tridecanol, etc. Ethoxylated tridecanols, which are especially preferably incorporated into the agents as contemplated herein, have proven to be particularly suitable. Particularly preferred agents as contemplated herein are characterized in that they contain—based on their weight—about 0.00001 to about 5% by weight, preferably about 0.0001 to about 3.5% by weight, especially preferably about 0.001 to about 2% by weight, more preferably about 0.01 to about 1% by weight and in particular about 0.1 to about 0.5% by weight branched ethoxylated tridecanoyl (INCI designation: trideceth-5-) or α-isotridecyl-ω-hydroxypolyglycol ether (INCI designation trideceth-10) or mixtures thereof.

The hair treatment agents as contemplated herein may contain vegetable oils, vegetable butters and/or vegetable waxes. These vegetable oil components in part improved combability and styleability to the hair and increase the sheen of hair.

The suitable vegetable oil components include natural (vegetable) oils and/or butters, which usually contain triglycerides and mixtures of triglycerides.

Preferred natural oils include coconut oil, (sweet) almond oil, walnut oil, peach kernel oil, apricot seed oil, argon oil, avocado oil, tea tree oil, soybean oil, sesame oil, sunflower oil, tsubaki oil, evening primrose oil, reiskleie oil, palm kernel oil, mango seed oil, marula oil, meadowlark oil, thistle oil, macadamia nut oil, grapeseed oil, amaranth seed oil, bamboo oil, olive oil, wheat germ oil, pumpkin seed oil, mallow oil, hazel nut oil, safflower oil, canola oil, sasanqua oil, jojoba oil, rambutan oil, cocoa butter and/or shea butter.

Preferably carnauba waxes, beeswax and/or candellila wax can be used as suitable natural or vegetable waxes.

Especially preferred vegetable oil components include (sweet) almond oil, peach kernel oil, apricot seed oil, amaranth seed oil, argan oil, olive oil, jojoba oil, cocoa butter and/or shea butter.

Particularly preferred are apricot seed oil, argan oil, olive oil and/orjojoba oil.

In a preferred embodiment the hair treatment agents as contemplated herein preferably contain coconut oil, (sweet) almond oil, walnut oil, peach kernel oil, apricot seed oil, argan oil, avocado oil, tea tree oil, soy oil, sesame oil, sunflower oil, Tsubaki (camellia) oil, evening primrose oil, rice bran oil, palm kernel oil, mango seed oil, marula oil, lady's smock (*Cardamine pratensis*) oil, thistle oil, macadamia nut oil, grape seed oil, amaranth seed oil, bamboo oil, olive oil, wheat germ oil, pumpkin seed oil, mallow oil, hazelnut oil, safflower oil, canola oil, sasanqua oil, jojoba oil, rambutan oil, cocoa butter and/or shea butter.

Within this embodiment, it is especially preferred if the hair treatment agents as contemplated herein contain (sweet) almond oil, peach kernel oil, apricot seed oil, amaranth seed oil, argan oil, olive oil, jojoba oil, cocoa butter and/or shea butter.

The amount by weight of the at least one vegetable oil, the vegetable butter and/or the vegetable wax in the total weight of the hair treatment agent as contemplated herein is preferably about 0.02 to about 2.50% by weight, more preferably from about 0.03 to about 2.00% by weight, especially preferably about 0.04 to about 1.50% by weight and in particular about 0.05 to about 1.00% by weight.

In another preferred embodiment, the hair treatment agent as contemplated herein may contain at least one additional hair conditioning active ingredient, in addition to the aforementioned essential and optional ingredients, to further increase the care properties of the agents. These additional ingredients may be selected from the group of
protein hydrolysates,
vitamins,
plant extracts and/or
glycerin.

Suitable protein hydrolysates are understood to be product mixtures which can be obtained by acidic, basic or enzymatically catalyzed degradation of proteins. Protein hydrolysates of vegetable, animal and/or marine origin may be used.

Animal protein hydrolysates include, for example, elastin, collagen, keratin, silk and milk protein hydrolysates which may also be present in the form of salts. Such products are distributed, for example, under the brand names Dehylan® (Cognis), Promois® (Interorgana), Collapuron® (Cognis), Nutrilan® (Cognis), Gelita-Sol (Deutsche Gelatine Fabriken Stoess & Co.), Lexein® (Inolex) and Kerasol® (Croda).

Preferred protein hydrolysates are those of plant origin, for example, soy, almond, rice, pea, potato and wheat protein hydrolysates. Such products are available, for example, under the brand names Gluadin® (Cognis), DiaMin® (Diamalt), Lexein® (Inolex) and Crotein® (Croda). Cationized protein hydrolysates can also be used in which the underlying protein hydrolysate may originate from an animal, for example, from collagen, milk or keratin, from a plant, for example, wheat, corn, rice, potatoes, soy or almonds, from marine life forms, for example, from fish collagen or algae or from protein hydrolysates obtained through biotechnology. The protein hydrolysates on which the cationic derivatives are based may be obtained from the corresponding proteins through a chemical in particular alkaline or acidic hydrolysis, by enzymatic hydrolysis and/or a combination of the two types of hydrolysis. Hydrolysis of proteins usually yields a protein hydrolysate with a molecular weight distribution of approx. 100 Dalton to several thousand Dalton. Such cationic protein hydrolysates whose underlying protein component has a molecular weight of about 100 up to about 25,000 Dalton, preferably about 250 to about 5000 Dalton are preferred. In addition cationic protein hydrolysates are understood to be quaternized amino acids and mixtures thereof. Quaternization of the protein hydrolysates or the amino acids is frequently carried out by means of quaternary ammonium salts such as N,N-dimethyl-N-(n-alkyl)-N-(2-hydroxy-3-chloro-n-propyl)ammonium halides, for example. In addition the cationic protein hydrolysates can also be further derivatized. Typical examples of cationic protein hydrolysates and derivative include products that are known by the following INCI designations and are available commercially: cocodimonium hydroxypropyl hydrolyzed collagen, cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed keratin, cocodimonium hydroxypropyl hydrolyzed rice protein, cocodimonium hydroxypropyl hydrolyzed silk, cocodimonium hydroxypropyl hydrolyzed soy protein, cocodimonium hydroxypropyl hydrolyzed wheat protein, cocodimonium hydroxypropyl silk amino acids, hydroxypropyl arginine lauryl/myristyl ether HCl, hydroxypropyltrimonium gelatin, hydroxypropyltrimonium hydrolyzed casein, hydroxypropyltrimonium hydrolyzed collagen, hydroxypropyltrimonium hydrolyzed conchiolin protein, hydroxypropyltrimonium hydrolyzed keratin, hydroxypropyltrimonium hydrolyzed rice bran protein, hydroxypropyltrimonium hydrolyzed silk, hydroxypropyltrimonium hydrolyzed soy protein, hydroxypropyl hydrolyzed vegetable protein, hydroxypropyltrimonium hydrolyzed wheat protein, hydroxypropyltrimonium hydrolyzed wheat protein/siloxysilicate, laurdimonium hydroxypropyl hydrolyzed soy protein, laurdimonium hydroxypropyl hydrolyzed wheat protein, laurdimonium hydroxypropyl hydrolyzed wheat protein/siloxysilicate, lauryldimonium hydroxypropyl hydrolyzed casein, lauryldimonium hydroxypropyl hydrolyzed collagen, lauryldimonium hydroxypropyl hydrolyzed keratin, lauryldimonium hydroxypropyl hydrolyzed silk, lauryldimonium hydroxypropyl hydrolyzed soy protein, steardimonium hydroxypropyl hydrolyzed casein, steardimonium hydroxypropyl hydrolyzed collagen, steardimonium hydroxypropyl hydrolyzed keratin, steardimonium hydroxypropyl hydrolyzed rice protein, steardimonium hydroxypropyl hydrolyzed silk, steardimonium hydroxypropyl hydrolyzed soy protein, steardimonium hydroxypropyl hydrolyzed vegetable protein, steardimonium hydroxypropyl hydrolyzed wheat protein, steartrimonium hydroxyethyl hydrolyzed collagen, quaternium-76 hydrolyzed collagen, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, quaternium-79 hydrolyzed wheat protein.

The amount by weight of the protein hydrolysate(s) in the total weight of the hair treatment agents is preferably about 0.01 to about 5% by weight, more preferably about 0.025 to about 3% by weight and in particular about 0.05 to about 2% by weight.

Regardless of the source (animal, vegetable, maritime, etc.), protein hydrolysates contain individual amino acids, oligopeptides and optionally polypeptides, depending on the degree of hydrolysis.

The hair treatment agents as contemplated herein especially preferably contain at least one oligopeptide having at least one Glu-Glu-Glu amino acid sequence, wherein the amino groups may be free or protonated and the carboxyl groups may be free or deprotonated.

Preferred hair treatment agents as contemplated herein are characterized in that they contain—based on their weight—about 0.001 to about 10% by weight of at least one oligopeptide having at least one Glu-Glu-Glu amino acid sequence, wherein the amino group may be free or protonated and the carboxyl groups may be free or deprotonated.

In this formula as well as in all the following formulas, the hydrogen atom of the amino group in parentheses as well as the hydroxyl group of the acid function in parentheses indicates that the respective groups may be present as such (then it is an oligopeptide having the respective number of amino acids, as indicated (i.e., 3 in the above formula) or that the amino acid sequence is present in an oligopeptides, which includes other amino acids as well—depending on where the additional amino acid(s) is (are) bound, the components of the above formula in parentheses are replaced by the additional amino acid radical(s). These preferred hair treatment agents as contemplated herein contain—based on their weight—about 0.0001 to about 10% by weight of at least one oligopeptide having at least one Glu-Glu-Glu amino acid sequence, i.e., at least three glutamic acids in succession.

Oligopeptides in the sense of the present patent application are condensation products of amino acids, which are linked by peptide bonds in the manner of an acid amide and which include at least three and at most 25 amino acids.

In preferred hair treatment agents as contemplated herein, the oligopeptide includes 5 to 15 amino acids, preferably 6 to 13 amino acids, especially preferably 7 to 12 amino acids and in particular 8, 9 or 10 amino acids.

Depending on whether additional amino acids are bound to the Glu-Glu-Glu sequence, and depending on the type of amino acids, the molecular weight of the oligopeptide contained in the agents as contemplated herein may vary. Preferred hair treatment agents used as contemplated herein are characterized in that the oligopeptide has a molecular weight of about 650 to about 3000 Da, preferably about 750 to about 2500 Da, especially preferably of about 850 to about 2000 Da and in particular of about 1000 to about 1600 Da.

In summary, preferred hair treatment agents are characterized in that the oligopeptide contains 5 to 15 amino acids, preferably 6 to 13 amino acids, especially preferably 7 to 12 amino acids and in particular 8, 9 or 10 amino acids and has a molecular weight of about 650 to about 3000 Da, preferably about 750 to about 2500 Da, especially preferably about 850 to about 2000 Da and in particular about 1000 to about 1600 Da.

As shown by the preferred number of amino acids in the oligopeptides and the preferred molecular mass range, the preferred oligopeptides are those that do not consists exclusively of the three glutamic acids but instead have additional amino acids bound to this sequence. These additional amino acids are preferably selected from certain amino acids whereas certain other representatives are less preferred as contemplated herein.

It is thus preferred if the oligopeptides used in the agents as contemplated herein do not contain any methionine.

It is additionally preferred if the oligopeptides used in the agents as contemplated herein do not contain any cysteine and/or cystine.

It is additionally preferred if the oligopeptides used in the agents as contemplated herein do not contain any aspartic acid and/or asparagine.

It is additionally preferred if the oligopeptides used in the agents as contemplated herein do not contain any serine and/or threonine.

On the other hand, it is preferred if the oligopeptides used in the agents as contemplated herein do contain tyrosine.

It is additionally preferred if the oligopeptides used in the agents as contemplated herein contain leucine.

It is additionally preferred if the oligopeptides used in the agents as contemplated herein contain isoleucine.

It is additionally preferred if the oligopeptides used in the agents as contemplated herein contain arginine.

It is additionally preferred if the oligopeptides used in the agents as contemplated herein contain valine.

Especially preferred oligopeptides and/or amino acid sequences contained in the preferred oligopeptides are described below:

A particularly preferred oligopeptide additionally contains tyrosine, which is preferably bound by its acid function to the Glu-Glu-Glu sequence. Hair treatment agents preferred as contemplated herein are therefore characterized in that the oligopeptide contained in them has at least one Tyr-Glu-Glu-Glu amino acid sequence, wherein the amino group may be free or protonated and the carboxyl groups may be free or deprotonated.

Another particularly preferred oligopeptide additionally contains isoleucine, which is preferably bound by its amino function to the Glu-Glu-Glu sequence. Preferred hair treatment agents as contemplated herein are therefore characterized in that the oligopeptide contained in them has at least one Glu-Glu-Glu-Ile amino acid sequence, wherein the amino group may be free or protonated and the carboxyl groups may be free or deprotonated.

Oligopeptides having both of the aforementioned amino acids (tyrosine and isoleucine) are preferred as contemplated herein.

Especially preferred are hair treatment agents as contemplated herein in which the oligopeptide contained in the hair treatment agent has at least one Tyr-Glu-Glu-Glu-Ile-Arg amino acid sequence, wherein the amino group may be free or protonated and the carboxyl groups may be free or deprotonated.

Further preferred oligopeptides additionally contain arginine, which is preferably bound to isoleucine.

Especially preferred are hair treatment agents as contemplated herein in which the oligopeptide contained in the hair treatment agent contains at least one Tyr-Glu-Glu-Glu-Ile-Arg amino acid sequence, wherein the amino groups may be free or protonated and the carboxyl groups may be free or deprotonated.

Even more preferred oligopeptides additionally contain valine, which is preferably bound to the arginine. Additionally preferred hair treatment agents as contemplated herein are therefore characterized in that the oligopeptide contained in the hair treatment agent has at least one Tyr-Glu-Glu-Glu-Ile-Arg-Va amino acid sequence, wherein the amino groups may be free or protonated and the carboxyl groups may be free or deprotonated.

Even further preferred oligopeptides additionally contain leucine, which is preferably bound to the valine. More preferred hair treatment agents as contemplated herein are therefore characterized in that the oligopeptide contained in the hair treatment agent has at least one Tyr-Glu-Glu-Glu-Ile-Arg-Va-Leu amino acid sequence, wherein the amino groups may be free or protonated and the carboxyl groups may be free or deprotonated.

Particularly preferred oligopeptides additionally contain leucine, which is preferably bound to the tyrosine. More preferred hair treatment agents as contemplated herein are therefore characterized in that the oligopeptide contained in the hair treatment agent has at least one Leu-Tyr-Glu-Glu-Glu-Ile-Arg-Val-Leu amino acid sequence, wherein the amino groups may be free or protonated and the carboxyl groups may be free or deprotonated.

Most especially preferably the agents as contemplated herein contain at least two oligopeptides, which meets the criteria defined above but are different from one another. Thus, for example, it is preferably to use hair treatment agents containing at least two different oligopeptides A and B both of which contain the Glu-Glu-Glu amino acid sequence.

Such differing oligopeptides A and B corresponding to one another in that they each have three successive Glu amino acids in their amino acid sequence but have differences in the amino acids bound upstream or downstream. Different peptides with partial agreement which may be much greater than that in the three amino acids mentioned above are preferred.

Thus additionally preferred hair treatment agents are characterized in that at least two different oligopeptides A and B, both of which contain the Glu-Glu-Glu-Ile amino acid sequence are contained in the hair treatment agent.

Also preferred are hair treatment agents that contain at least two oligopeptides A and B but are different from one another, both of them containing the Tyr-Glu-Glu-Glu amino acid sequence.

Even more preferred hair treatment agents are characterized in that they contain at least two different oligopeptides A and B, both of which have the Glu-Glu-Glu-Ile-Arg amino acid sequence.

Also more preferred hair treatment agents are characterized in that the hair treatment agent contains at least two different oligopeptides A and B, both of which have the Tyr-Glu-Glu-Glu-Ile amino acid sequence.

Hair treatment agents preferred as contemplated herein are therefore characterized in that the oligopeptide has at least one Tyr-Glu-Glu-Glu-Ile amino acid sequence, wherein the amino group may be free or protonated and the carboxyl groups may be free or deprotonated.

Most especially preferred hair treatment agents are characterized in that the hair treatment agent contains at least two different oligopeptides A and B, both of which contain the Glu-Glu-Glu-Ile-Arg amino acid sequence.

Hair treatment agents that are also especially preferred are characterized in that the hair treatment agent contains at least one two different oligopeptides A and B, both of which have the Tyr-Glu-Glu-Glu-Ile-Arg amino acid sequence.

There is preferably an even greater structural correspondence in the oligopeptides. Thus hair treatment agents containing at least two different oligopeptides A and B, both of which have the Glu-Glu-Glu-Ile-Arg-Val amino acid sequence are additional preferred embodiments as contemplated herein.

Embodiments of the hair treatment agent that are also preferred contain at least two different oligopeptides A and B both of which have the Tyr-Glu-Glu-Glu-Ile-Arg-Val amino acid sequence.

Even more preferred hair treatment agents as contemplated herein are characterized in that they contain at least two different oligopeptides A and B, both of which have the Glu-Glu-Glu-Ile-Arg-Val-Leu amino acid sequence.

Hair treatment agents as contemplated herein that are even more preferred are characterized in that they contain at least two different oligopeptides A and B, both of which have the Tyr-Glu-Glu-Glu-Ile-Arg-Val amino acid sequence.

Hair treatment agents that are preferred as contemplated herein are therefore characterized in that the oligopeptide has at least one Tyr-Glu-Glu-Glu-Ile-Arg-Val-Leu amino acid sequence, wherein the amino groups may be free or protonated and the carboxyl groups may be free or deprotonated.

In particular preferred hair treatment agents as contemplated herein are characterized in that they contain at least two different oligopeptides A and B, wherein the oligopeptide A has the Leu-Tyr-Glu-Glu-Glu-Ile-Arg-Va-Leu amino acid sequence, wherein the amino groups may be free or protonated and the carboxyl groups may be free or deprotonated, and oligopeptide B has the Tyr-Glu-Glu-Glu-Ile-Arg-Va-Leu amino acid sequence, wherein the amino groups may be free or protonated and the carboxyl groups may be free or deprotonated.

In most especially preferred hair treatment agents of this latter embodiment, they contain—based on the weight of the agent—about 0.00001 to about 1% by weight oligopeptide A and about 0.00001 to about 1% by weight oligopeptide B.

In more preferred hair treatment agents of this latter embodiment, they contain—based on the weight of the agent—about 0.00005 to about 0.1% by weight oligopeptide A and about 0.00005 to about 0.1% by weight oligopeptide B.

In even more preferred hair treatment agents of this latter embodiment, they contain based on the weight of the agent about 0.0001 to about 0.01% by weight oligopeptide A and about 0.0001 to about 0.001% by weight oligopeptide B.

The oligopeptides which meet the conditions defined above and are used within the scope as contemplated herein may advantageously be derived from keratinic materials. It is preferred as contemplated herein that these oligopeptides are used in large amounts, based on the total keratinic peptide content of the agents.

It is most especially preferable for the highest possible amount of all keratinic peptides contained in the agent as contemplated herein to meet the conditions defined above. Preferred hair treatment agents as contemplated herein are characterized in that they contain at least about 0.1% by weight, preferably at least about 0.5% by weight, especially preferably at least about 1% by weight, more preferably at least about 2.5% by weight, even more preferably at least about 5% by weight and in particular at least about 10% by weight of all the keratinic peptides, which have the Glu-Glu-Glu amino acid sequence and are contained in the agent.

More preferred hair treatment agents as contemplated herein are characterized in that at least about 0.1% by weight, preferably at least about 0.5% by weight, especially preferably at least about 1% by weight, more preferably at least about 2.5% by weight, even more preferably at least about 5% by weight and in particular at least about 10% by weight of all keratinic peptides contained in the agent have the Glu-Glu-Glu-Ile amino acid sequence.

Even more preferred hair treatment agents as contemplated herein are characterized in that at least about 0.1% by weight, preferably at least about 0.5% by weight, especially preferably at least about 1% by weight, more preferably at least about 2.5% by weight, even more preferably at least about 5% by weight and in particular at least about 10% by weight of all keratinic peptides contained in the agent have the Tyr-Glu-Glu-Glu amino acid sequence.

Especially preferred hair treatment agents as contemplated herein are characterized in that at least about 0.1% by weight, preferably at least about 0.5% by weight, especially preferably at least about 1% by weight, more preferably at least about 2.5% by weight, even more preferably at least about 5% by weight and in particular at least about 10% by weight of all keratinic peptides contained in the agent have the Tyr-Glu-Glu-Glu-Ile amino acid sequence.

Most especially preferred hair treatment agents as contemplated herein are characterized in that at least about 0.1% by weight, preferably at least about 0.5% by weight, especially preferably at least about 1% by weight, more preferably at least about 2.5% by weight, even more preferably at least about 5% by weight and in particular at least about 10% by weight of all keratinic peptides contained in the agent have the Tyr-Glu-Glu-Glu-Ile-Arg amino acid sequence.

Even more preferred hair treatment agents as contemplated herein are characterized in that at least about 0.1% by weight, preferably at least about 0.5% by weight, especially preferably at least about 1% by weight, more preferably at least about 2.5% by weight, even more preferably at least about 5% by weight and in particular at least about 10% by weight of all keratinic peptides contained in the agent have the Tyr-Glu-Glu-Glu-Ile-Arg-Val amino acid sequence.

Particularly preferred hair treatment agents as contemplated herein are characterized in that at least about 0.1% by weight, preferably at least about 0.5% by weight, especially preferably at least about 1% by weight, more preferably at least about 2.5% by weight, even more preferably at least about 5% by weight and in particular at least about 10% by weight of all keratinic peptides contained in the agent have the Tyr-Glu-Glu-Glu-Ile-Arg-Val-Leu amino acid sequence.

The conditions defined above relate to the total peptide content of the agents as contemplated herein originating from keratinic materials. In addition to the oligopeptides of keratinic origin, additional peptides and/or protein hydrolysates may of course be used, for example, those from other native sources. For example, the additional use of wheat protein hydrolysates is preferred.

Of suitable vitamins, the following vitamins, provitamins and vitamin precursors as well as derivatives thereof are to be understood:

Vitamin A: The group of substances known as vitamin A include retinol (vitamin $A_1$) and 3,4-didehydroretinol (vitamin $A_2$). The β-carotene is the provitamins of retinol. Vitamin A components that may be considered include, for example, vitamin A acid and esters thereof, vitamin A aldehyde and vitamin A alcohol as well as esters thereof such as the palmitate and the acetate.

Vitamin B: the vitamin B group or the B complex includes among others

Vitamin $B_1$ (thiamine)

Vitamin $B_2$ (riboflavin)

Vitamin $B_3$. This designation often includes the compounds nicotinic acid and nicotinamide (niacinamide).

Vitamin $B_5$ (pantothenic acid and panthenol). Panthenol is preferably used within the context of this group. Derivatives of panthenol that can be used include in particular the esters and ethers of panthenol, pantolactone as well as cationically derivatized panthenols. Individual representatives include, for example, panthenol triacetate, panthenol monoethyl ether and its monoacetate as well as cationic panthenol derivatives.

Vitamin B$_6$ (pyridoxine as well as pyridoxamine and pyridoxal)

Vitamin C (ascorbic acid): Use in the form of palmitic acid ester, glucosides or phosphates may be preferred. Use in combination with tocopherols may also be preferred.

Vitamin E (tocopherols, in particular α-tocopherol)

Vitamin F: The term "vitamin F" is usually understood to refer to essential fatty acids, in particular linoleic acid, linolenic acid and arachidonic acid.

Vitamin H: Vitamin H refers to the compound (3aS,4S,6aR)-2-oxohexahydrothienol-[3,4-d]-imidazole-4-valeric acid, but the trivial name biotin has become popular for this compound in the meantime.

Vitamins, provitamins and vitamin precursors from groups A, B, E and H are especially preferred. Preferred in particular are nicotinamide, biotin, pantolactone and/or panthenol.

The amount by weight of the vitamin(s), vitamin derivative(s) and/or vitamin precursor(s) in the total weight of the hair treatment agent is preferably about 0.001 to about 2% by weight, especially preferably about 0.005 to about 1% by weight and in particular about 0.01 to about 0.5% by weight.

Suitable plant extracts are understood to be extracts that can be produced from all parts of a plant. These extracts are usually produced by extraction of the total plant but in individual cases it may also be preferable to produce the extracts exclusively from the blossoms and/or leaves of the plant. Suitable extracts in particular include extracts of green tea, oak bark, stinging nettle, witch hazel, hops, chamomile, burdock root, horsetail, hawthorn, lime blossom, lychee, almond, aloe vera, spruce needle, horse chestnut, sandalwood, juniper, coconut, mango, apricot, lime, wheat, kiwi, melon, orange, grapefruit, sage, rosemary, birch, mallows, *Cardamine pratensis* (lady's smock, meadow cardamine), wild thyme, yarrow, thyme, sweet balm, restharrow (*Ononis spinosa*), coltsfoot, mallow, ginseng, ginger root, *Echinacea purpurea*, olive (*Olea europea*), *Boerhavia diffusa* root, *Foeniculum* vulgaris and celery (*Apim graveolens*).

Especially preferred for use in the compositions as contemplated herein are the extracts of green tea, stinging nettle, witch hazel, chamomile, aloe vera, *ginseng, Echinacea purpurea, Olea europea* and/or *Boerhavia diffusa* root.

Extraction agents for producing the aforementioned plant extracts may include water, alcohols, as well as mixture thereof. Suitable alcohols include lower alcohols such as ethanol and isopropanol, but in particular polyvalent alcohols such as ethylene glycol and propylene glycol are preferred either as the sole extraction agent or in mixture with water. Plant extracts based on water-propylene glycol in a 1:10 ratio to a 10:1 ratio have proven to be particularly suitable.

The plant extracts may be used in pure or diluted form. If they are used in diluted form, they usually contain approx. 2-80% by weight active substance and, as the solvent, the extraction agent or extraction agent mixture used to produce them.

The plant extracts may preferably be used in the hair treatment agents as contemplated herein (based on the total weight of the agents) in an amount from about 0.01 to about 10% by weight, more preferably from about 0.05 to about 7.5% by weight and in particular from about 0.1 to about 5% by weight.

Glycerin may be added to the hair cleaning and care agents separately in an amount of up to about 10% by weight (based on the total weight of the agent). However, it may also be an ingredient of the aforementioned aqueous alcoholic vehicle.

It has been found that the hair treatment agents as contemplated herein are also suitable for use as an antidandruff preparation.

The total weight of the antidandruff agents in the total weight of the hair treatment agent may preferably be about 0.01 to about 10% by weight, more preferably about 0.025 to about 7.5% by weight, especially preferably about 0.05 to about 5% by weight and in particular about 0.075 to about 3% by weight.

Suitable antidandruff active ingredients can be selected from piroctone olamine, climbazole, zinc pyrithione, ketoconazoles, salicylic acid, sulfur, selenium sulfide, tar preparations, undecanoic acid derivatives, burdock root extracts, poplar extracts, stinging nettle extracts, walnut shell extracts, birch extracts, willow bark extracts, rosemary extracts and/or *arnica* extracts.

Preferred are climbazole, zinc pyrithione and piroctone olamine.

Additional active ingredients, auxiliaries and additives that may preferably be contained in the hair treatment agents as contemplated herein include, for example:

humectants,
perfumes,
UV filters,
thickeners such as gelatin or plant gums, for example, agar, guar gum, alginates, xanthan gum, gum arabic, karaya gum, carob powder, linseed gums, dextrins, cellulose derivatives, for example, methyl cellulose, hydroxyalkyl cellulose and carboxymethyl cellulose, starch fractions and derivatives such as amylose, amylopectin and dextrins, clays and sheet silicates such as bentonite or completely synthetic hydrocolloids such as polyvinyl alcohol, the Ca, Mg or Zn soaps,
structurants, such as maleic acid and lactic acid,
dimethyl isosorbide,
cyclodextrins,
fiber-structure-improving active ingredients, in particular mono-, di- and oligosaccharides, such as, for example, glucose, galactose, fructose, fruit sugar and lactose,
dyes for coloring the agent,
complexing agents such as EDTA, NTA, β-alanine diacetic acid and phosphonic acids,
propellants such as propane-butane mixtures, N$_2$O, dimethyl ether, CO$_2$ and air,
antioxidants,
additional viscosity regulators such as salts (NaCl).

The agents as contemplated herein are preferably so-called rinse-off products, i.e., they are rinsed out of the hair after a certain treatment time. This treatment time preferably amounts to less than about 1 hour, i.e., the user preferably does not leave the products in his/her hair until the next shampooing.

Another subject matter as contemplated herein is therefore a method for treating hair, in which an agent as contemplated herein is applied to dry or damp hair, left there for a period of about 30 to about 300 seconds and then rinsed out.

The agents as contemplated herein lead to a definitely increased stability of artificial dyeings with respect to the fading of color. Chemically dyed hair can therefore definitely be washed more often with the agents as contemplated herein without resulting in any unwanted leaching or fading of the color.

Another subject matter as contemplated herein is therefore the use of agents as contemplated herein for reducing the fading of color from chemically dyed hair.

With regard to preferred embodiment of the method as contemplated herein and the use as contemplated herein, what was said about the agents as contemplated herein also applies here, mutatis mutandis.

EXAMPLES

All amounts given in percent % by weight

| Hair treatments | 1 | 2 | 3 | 4 | 5 | 6 |
|---|---|---|---|---|---|---|
| Cetearyl alcohol | 7.0 | 7.0 | 7.0 | 7.0 | 7.0 | 7.0 |
| Quaternium-87 | 0.9 | 0.9 | 0.9 | 0.9 | 0.9 | 0.9 |
| Cetrimonium chloride | 1.5 | 1.5 | 1.5 | 1.5 | 1.5 | 1.5 |
| Distearoylethyl hydroxyethyl-monium methosulfate | 2.0 | 2.0 | 2.0 | 2.0 | 2.0 | 2.0 |
| Polyquaternium-10 | 0.1 | 0.1 | 0.1 | 0.1 | 0.1 | 0.1 |
| Baobab seed oil | 0.1 | 0.1 | 0.1 | 0.1 | 0.1 | 0.1 |
| Polyquaternium-37 | 0.4 | 0.4 | 0.4 | 0.4 | 0.4 | 0.4 |
| Hydrolyzed keratin | 0.5 | 0.5 | 0.5 | 0.5 | 0.5 | 0.5 |
| Glycol distearate | 1.0 | 1.0 | 1.0 | 1.0 | 1.0 | 1.0 |
| Silver citrate | 0.1 | 0.1 | 0.1 | 0.1 | 0.1 | 0.1 |
| Citric acid | 1.5 | 1.5 | 1.5 | 1.5 | 1.5 | 1.5 |
| Dimethicone | 1.0 | 1.0 | 1.0 | 1.0 | 1.0 | 1.0 |
| Calcium chloride | 1.0 | 1.0 | 1.0 | 1.0 | 1.0 | 1.0 |
| Propionic acid | — | 0.2 | 0.2 | 0.2 | 0.2 | 0.2 |
| o-Phenyl phenol | — | 0.2 | 0.2 | 0.2 | 0.2 | 0.2 |
| o-Cymen-5-ol | — | 0.06 | 0.06 | 0.06 | 0.06 | 0.06 |
| Ethyl lauroyl arginate | — | 0.3 | 0.3 | 0.3 | 0.3 | 0.3 |
| Dimethyloxazolidine | — | 0.05 | 0.06 | 0.07 | 0.08 | 0.1 |
| Ethyl lauroyl arginate | — | 0.4 | 0.3 | 0.2 | 0.1 | 0.05 |
| Glutaraldehyde | — | 0.05 | 0.06 | 0.07 | 0.08 | 0.1 |
| Hexetidine | — | 0.05 | 0.06 | 0.07 | 0.08 | 0.1 |
| Phenoxyethanol | — | 0.05 | 0.05 | 0.05 | 0.05 | 0.05 |
| Phenoxyisopropanol | — | 0.05 | 0.1 | 0.25 | 0.05 | 0.05 |
| Undecylenic acid | — | 0.1 | 0.2 | 0.1 | 0.2 | 0.1 |
| Dye | 0.2 | 0.2 | 0.2 | 0.2 | 0.2 | 0.2 |
| Perfume | 0.1 | 0.1 | 0.1 | 0.1 | 0.1 | 0.1 |
| Water | to a total of 100 | | | | | |

| Hair rinses | 1 | 2 | 3 | 4 | 5 | 6 |
|---|---|---|---|---|---|---|
| Cetearyl alcohol | 5.0 | 5.0 | 5.0 | 5.0 | 5.0 | 5.0 |
| Quaternium-87 | 0.75 | 0.75 | 0.75 | 0.75 | 0.75 | 0.75 |
| Behentrimonium chloride | 1.0 | 1.0 | 1.0 | 1.0 | 1.0 | 1.0 |
| Behenoyl PG trimonium chloride | 1.5 | 1.5 | 1.5 | 1.5 | 1.5 | 1.5 |
| Glycol distearate | 1.0 | 1.0 | 1.0 | 1.0 | 1.0 | 1.0 |
| Distearoylethyl hydroxyethyl-monium methosulfate | 0.3 | 0.3 | 0.3 | 0.3 | 0.3 | 0.3 |
| Amodimethicone/morpholinomethyl silsesquioxane copolymer | 0.1 | 0.1 | 0.1 | 0.1 | 0.1 | 0.1 |
| Silver citrate | 0.3 | 0.3 | 0.3 | 0.3 | 0.3 | 0.3 |
| Citric acid | 0.5 | 0.5 | 0.5 | 0.5 | 0.5 | 0.5 |
| Shea butter | 1.5 | 1.5 | 1.5 | 1.5 | 1.5 | 1.5 |
| Lactic acid | 0.1 | 0.1 | 0.1 | 0.1 | 0.1 | 0.1 |
| Magnesium chloride | 0.5 | 0.5 | 0.5 | 0.5 | 0.5 | 0.5 |
| Sodium propionate | — | 0.5 | 0.5 | 0.5 | 0.5 | 0.5 |
| Phenoxyethanol | — | 0.5 | 0.5 | 0.5 | 0.5 | 0.5 |
| Dimethyloxazolidine | — | 0.05 | 0.06 | 0.07 | 0.08 | 0.1 |
| Glutaraldehyde | — | 0.05 | 0.06 | 0.07 | 0.08 | 0.1 |
| Hexetidine | — | 0.05 | 0.06 | 0.07 | 0.08 | 0.1 |
| Ethyl lauroyl arginate | — | 0.05 | 0.05 | 0.05 | 0.05 | 0.05 |
| Sodium-o-phenylphenolate | — | 1.0 | 0.5 | 0.25 | 0.2 | 0.1 |
| o-Cymen-5-ol | — | 0.2 | 0.1 | 0.2 | 0.1 | 0.1 |
| Phenoxyisopropanol | — | 0.05 | 0.1 | 0.25 | 0.05 | 0.05 |
| Undecylenic acid | — | 0.1 | 0.2 | 0.1 | 0.2 | 0.1 |
| Dye | 0.2 | 0.2 | 0.2 | 0.2 | 0.2 | 0.2 |
| Perfume | 0.1 | 0.1 | 0.1 | 0.1 | 0.1 | 0.1 |
| Water | to a total of 100 | | | | | |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment. It being understood that various changes may be made in the function and arrangement of elements described in an exemplary embodiment without departing from the scope as set forth in the appended claims.

The invention claimed is:

1. A hair treatment agent consisting of, based on the total weight of the hair treatment agent:
 a) 7.0% by weight of cetearyl alcohol;
 b) 0.9% by weight of quaternium-87;
 c) 1.5% by weight of cetrimonium chloride;
 d) 2.0% by weight of distearolyethyl hydroxyethylmonium methosulfate;
 e) 0.1% by weight of polyquaternium-10;
 f) 0.1% by weight of baobab seed oil;
 g) 0.4% by weight of polyquaternium-37;
 h) 0.5% by weight of hydrolyzed keratin;
 i) 1.0% by weight of glycol distearate;
 j) 0.1% by weight of silver citrate;
 k) 1.5% by weight of citric acid;
 l) 1.0% by weight of dimethicone;
 m) 1.0% by weight calcium chloride;
 n) 0.2% by weight of dye;
 o) 0.1% by weight of perfume; and
 p) water;
and optionally one or more of:
 q) propionic acid;
 r) o-phenylphenol;
 s) o-cymen-5-ol;
 t) ethyl lauroyl arginate;
 u) dimethyloxazolidine;
 v) glutaraldehyde;
 w) hexetidine;
 x) phenoxyethanol;
 y) phenoxyisopropanol; and
 z) undecylenic acid.

2. A hair treatment agent consisting of, based on the total weight of the hair treatment agent:
 a) 5.0% by weight of cetearyl alcohol;
 b) 0.75% by weight of quaternium-87;
 c) 1.0% by weight of behentrimonium chloride;
 d) 1.5% by weight of behenoyl PG-trimonium chloride;
 e) 1.0% by weight of glycol distearate;
 f) 0.3% by weight of distearoylethyl hydroxyethylmonium methosulfate;
 g) 0.1% by weight of amodimethicone/morpholinomethyl silsesquioxane copolymer;
 h) 0.3% by weight of silver citrate;
 i) 0.5% by weight of citric acid;
 j) 1.5% by weight of shea butter;
 k) 0.1% by weight of lactic acid;
 l) 0.5% by weight of magnesium chloride;
 m) 0.2% by weight of dye;
 n) 0.1% by weight of perfume; and
 o) water;
and optionally one or more of:
 p) sodium propionate;
 q) phenoxyethanol;
 r) dimethyloxazolidine;
 s) glutaraldehyde;
 t) hexetidine;

u) ethyl lauroyl arginate;
v) sodium-o-phenylphenolate;
w) o-cymen-5-ol;
x) phenoxyisopropanol; and
y) undecylenic acid.

* * * * *

SEQUENCE LISTING

```
<160> NUMBER OF SEQ ID NOS: 11

<210> SEQ ID NO 1
<211> LENGTH: 3
<212> TYPE: PRT
<213> ORGANISM: Artificial
<220> FEATURE:
<223> OTHER INFORMATION: Peptide

<400> SEQUENCE: 1

Glu Glu Glu
1

<210> SEQ ID NO 2
<211> LENGTH: 4
<212> TYPE: PRT
<213> ORGANISM: Artificial
<220> FEATURE:
<223> OTHER INFORMATION: Peptide
```

```
<400> SEQUENCE: 2

Tyr Glu Glu Glu
1

<210> SEQ ID NO 3
<211> LENGTH: 4
<212> TYPE: PRT
<213> ORGANISM: Artificial
<220> FEATURE:
<223> OTHER INFORMATION: Peptide

<400> SEQUENCE: 3

Glu Glu Glu Ile
1

<210> SEQ ID NO 4
<211> LENGTH: 6
<212> TYPE: PRT
<213> ORGANISM: Artificial
<220> FEATURE:
<223> OTHER INFORMATION: Peptide

<400> SEQUENCE: 4

Tyr Glu Glu Glu Ile Arg
1               5

<210> SEQ ID NO 5
<211> LENGTH: 7
<212> TYPE: PRT
<213> ORGANISM: Artificial
<220> FEATURE:
<223> OTHER INFORMATION: Peptide

<400> SEQUENCE: 5

Tyr Glu Glu Glu Ile Arg Val
1               5

<210> SEQ ID NO 6
<211> LENGTH: 8
<212> TYPE: PRT
<213> ORGANISM: Artificial
<220> FEATURE:
<223> OTHER INFORMATION: Peptide

<400> SEQUENCE: 6

Tyr Glu Glu Glu Ile Arg Val Leu
1               5

<210> SEQ ID NO 7
<211> LENGTH: 9
<212> TYPE: PRT
<213> ORGANISM: Artificial
<220> FEATURE:
<223> OTHER INFORMATION: Peptide

<400> SEQUENCE: 7

Leu Tyr Glu Glu Glu Ile Arg Val Leu
1               5

<210> SEQ ID NO 8
<211> LENGTH: 5
<212> TYPE: PRT
<213> ORGANISM: Artificial
<220> FEATURE:
<223> OTHER INFORMATION: Peptide
```

```
-continued

<400> SEQUENCE: 8

Glu Glu Glu Ile Arg
1               5

<210> SEQ ID NO 9
<211> LENGTH: 5
<212> TYPE: PRT
<213> ORGANISM: Artificial
<220> FEATURE:
<223> OTHER INFORMATION: Peptide

<400> SEQUENCE: 9

Tyr Glu Glu Glu Ile
1               5

<210> SEQ ID NO 10
<211> LENGTH: 6
<212> TYPE: PRT
<213> ORGANISM: Artificial
<220> FEATURE:
<223> OTHER INFORMATION: Peptide

<400> SEQUENCE: 10

Glu Glu Glu Ile Arg Val
1               5

<210> SEQ ID NO 11
<211> LENGTH: 7
<212> TYPE: PRT
<213> ORGANISM: Artificial
<220> FEATURE:
<223> OTHER INFORMATION: Peptide

<400> SEQUENCE: 11

Glu Glu Glu Ile Arg Val Leu
1               5
```